(12) United States Patent
Anderson et al.

(10) Patent No.: US 8,946,149 B2
(45) Date of Patent: Feb. 3, 2015

(54) USE OF EXENDIN AND ANALOGS THEREOF TO DELAY OR PREVENT CARDIAC REMODELING

(75) Inventors: Christen Anderson, Encinitas, CA (US); Que Liu, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 1198 days.

(21) Appl. No.: 11/910,730

(22) PCT Filed: Apr. 11, 2006

(86) PCT No.: PCT/US2006/013949
§ 371 (c)(1),
(2), (4) Date: Jun. 20, 2008

(87) PCT Pub. No.: WO2006/110887
PCT Pub. Date: Oct. 19, 2006

(65) Prior Publication Data
US 2009/0137466 A1 May 28, 2009

Related U.S. Application Data

(60) Provisional application No. 60/669,876, filed on Apr. 11, 2005.

(51) Int. Cl.
*A61K 38/26* (2006.01)
*A61P 9/10* (2006.01)
*A61K 38/22* (2006.01)
*C07K 14/605* (2006.01)

(52) U.S. Cl.
CPC ............. *A61K 38/26* (2013.01); *A61K 38/2278* (2013.01)
USPC ............................ 514/7.2; 514/16.4; 530/308

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 5,118,666 A | 6/1992 | Habener | |
| 5,424,286 A | 6/1995 | Eng | |
| 5,512,549 A | 4/1996 | Chen | |
| 6,006,753 A | 12/1999 | Efendic | |
| 6,277,819 B1 | 8/2001 | Efendic | |
| 6,284,725 B1 | 9/2001 | Coolidge et al. | |
| 6,703,359 B1 | 3/2004 | Young et al. | |
| 6,706,689 B2 | 3/2004 | Coolidge et al. | |
| 6,747,006 B2 | 6/2004 | Efendic | |
| 6,894,024 B2 | 5/2005 | Coolidge et al. | |
| 7,056,887 B2 | 6/2006 | Coolidge et al. | |
| 7,101,843 B2 | 9/2006 | Glaesner et al. | |
| 7,186,692 B2 | 3/2007 | Quay | |
| 7,192,922 B2 | 3/2007 | Shannon et al. | |
| 7,259,233 B2 | 8/2007 | Dodd et al. | |
| 7,442,680 B2 | 10/2008 | Young et al. | |
| 7,446,091 B2 | 11/2008 | Van Den Berghe | |
| 2003/0199445 A1 | 10/2003 | Knudsen et al. | |
| 2003/0220255 A1 | 11/2003 | Knudsen et al. | |
| 2004/0208929 A1 | 10/2004 | Costantino | |
| 2004/0228833 A1 | 11/2004 | Costantino | |
| 2004/0266683 A1 | 12/2004 | Hathaway et al. | |
| 2005/0031549 A1 | 2/2005 | Quay | |
| 2007/0021336 A1 | 1/2007 | Anderson et al. | |
| 2008/0015144 A1 | 1/2008 | Brownlee | |
| 2010/0029554 A1* | 2/2010 | Ghosh et al. | 514/12 |

FOREIGN PATENT DOCUMENTS

| | | |
|---|---|---|
| EP | 0708179 | 4/1996 |
| EP | 1512410 | 3/2005 |
| WO | WO 91/11457 | 8/1991 |
| WO | WO 99/07404 | 2/1999 |
| WO | WO 99/25727 | 5/1999 |
| WO | WO 99/25728 | 5/1999 |
| WO | WO 99/40788 | 8/1999 |
| WO | WO 01/89554 | 11/2001 |
| WO | WO 03/084563 | 10/2003 |
| WO | WO 2004/056313 | 7/2004 |
| WO | WO 2005/000222 | 1/2005 |

OTHER PUBLICATIONS

Pohl et al 1998. Journal of Biochemistry. 273(16): 9778-9784).*
Hargrove et al, 2007. Regulatory Peptides. 141: 113-119.*
Yousef et al, 2000. Cardiovascular Drugs and Therapy. 14: 243-252.*
Liu et al., J. Cardiac Failure 11(6):S95 (Aug. 2005) "Chronic Treatment with GLP-1 Improves Cardiac Function, Delays Cardiac Remodeling and Enhances Exercise Performance . . . ".
Sharpe, Current Heart Failure Reports 1(1):9-13 (Apr. 2004) "Pharmacologic Effects on Cardiac Remodeling".
Nikolaidis et al., "Effects of Glucagon-Like Peptide-1 in Patients With Acute Myocardial Infarction and Left Ventricular Dysfunction . . . " Circulation 2004;109;962-965.
Nikolaidis et al., "Active metabolite of GLP-1 mediates myocardial glucose uptake and improves left ventrical . . . ," Am J Physiol Heart Circ Physiol 289: H2401-H2408, 2005.
Adelhorst, et al., J. Biol. Chem. 269(9): 6275-6278 (1994).
Balkan, B., et al., Diabetologia 42(11):1324-1331 (1999).
Bose, et al., Diabetes 54: 146-151 (2005).
Buteau, Diabetologica 42:856-864 (1999).
D'Alessio, et al., J. Clin. Invest., 97:133-38 (1996).

(Continued)

*Primary Examiner* — Zachary Howard
(74) *Attorney, Agent, or Firm* — Womble Carlyle Sandridge & Rice, LLP

(57) ABSTRACT

The present invention relates generally to the novel use of cardioprotective incretin compounds (CICs) such as GLP-1 and exendin and agonists thereof, including analogs and derivatives to prevent, delay, attenuate, or ameliorate cardiac remodeling. The present invention relates to methods for using CICs for the treatment of conditions associated with cardiac remodeling. The present invention further relates to methods for using CICs for the reduction of the risk or severity of congestive heart failure.

24 Claims, 15 Drawing Sheets

(56) References Cited

OTHER PUBLICATIONS

Deacon, et al., 16th International Diabetes Federation Congress Abstracts, Diabetologia Supplement[1] (1997) vol. 40, p. A127.
Drucker, Diabetes 47: 159-169 (1998).
Drucker, Endocrinology 144(12):5145-5148 (2003).
Edmondson, S.D., et al., Bioorg. Med. Chem. Lett. 14(20): 5151-5155 (2004).
Eissele, et al., Life Sci., 55:629-34 (1994).
Fedak, Cardiovascular Pathology 14:1-11 (2005).
Fehmann, H.C., et al., Peptides, 15 (3): 453-6 (1994).
Ferraris, D., et al., Bioorg. Med. Chem. Lett. 14(22): 5579-5583 (2004).
Fortuno, Hypertension 38: 1406-1412 (2001).
Fukushima, H., et al., Bioorg. Med. Chem. Lett. 14(22): 6053-6061 (2004).
Goke, et al., J. Biol. Chem., 268:19650-55 (1993).
Goke, et al., Diabetic Medicine 13: 854 860 (1996).
Hareter, et al., Amer. Diabetes Assoc. 57th Scientific Sessions, Boston (1997).
Hjorth, et al., J. Biol. Chem. 269(48): 30121-30124 (1994).
Holz, et al., Comparative Biochemistry and Physiology, Part B, 121: 177 184 (1998).
Irwin, et al., Proc. Natl. Acad. Sci. USA. 94: 7915 7920 (1997).
Kenhard, J.M., et al., Biochem. Biophys. Res. Commun. 324(1):92-97 (2004).
Kyte and Doolittle, J. Mol. Biol. 157:105-132 (1982).
Malhotra, R., et al., Regulatory Peptides, 41:149-56 (1992).
Marguet, D., et al., Proc. Natl. Acad. Sci. USA 97(12): 6874-6879 (2000).
Mentlein, R., et al., Eur. J. Biochem., 214:829-835 (1993).
Montrose-Rafizadeh, et al., Diabetes, 45(Suppl. 2):152A (1996).
Mosjov, Int. J Peptide Protein Res. 40: 333 343 (1992).
Pederson, R. A., et al., Diabetes 47: 1253-1258 (1998).
Raufman, J. P., et al., J. Biol. Chem., 266:2897-902 (1991).
Raufman, J.P., et al., J. Biol. Chem., 267:21432-37 (1992).
Ritzel, et al., "A synthetic glucagon-like peptide-1 analog with improved plasma stability," J. Endocrinol. 159(1): 93 102 (1998).
Schepp, W., et al., Eur. J. Pharm., 269:183-91 (1994).
Siegel, et al., Amer. Diabetes Assoc.57th Scientific Sessions, Boston (1997).
Singh, et al., Regul. Pept., 53:47-59 (1994).
Somasundaram, Med. Clin. N. Am., 88: 1193-1207 (2004).
Thorens, B., Proc. Natl. Acad. Sci. USA 89:8641-8645 (1992).
Thorens, B., et al., Diabetes, 42 (11): 1678-82 (1993).
Wang, et al., J. Clin. Invest., 95:417-21 (1995).

* cited by examiner

\* p<0.05 compared with other groups

FIGURE 9-A

```
1                                     5                  10                  15                  20
Xaa1 Xaa2 Xaa3 Gly Thr Xaa6 Xaa7 Xaa8 Xaa9 Xaa10 Ser Lys Gln Xaa14 Glu Glu Glu Ala Val Arg Leu
             25                  30                  35
Xaa22 Xaa23 Xaa24 Xaa25 Leu Lys Asn Gly Gly Xaa31 Ser Ser Gly Ala Xaa36 Xaa37 Xaa38 Xaa39-Z
```

| # | 1 | 2 | 3 | 4 | 5 | 6 | 7 | 8 | 9 | 10 | 11 | 12 | 13 | 14 | 15 | 16 | 17 | 18 | C-term |
|---|---|---|---|---|---|---|---|---|---|----|----|----|----|----|----|----|----|----|--------|
| [9]  | His | Gly | Glu  | Phe  | Thr | Ser | Asp | Leu  | Leu  | Phe | Ile | Glu | Phe | Pro | Pro | Pro | Pro | Ser | NH₂ |
| [10] | His | Gly | Glu  | Phe  | Thr | Ser | Asp | Leu  | Leu  | Phe | Ile | Glu | Trp | Pro | Pro | Pro | Pro | Ser | NH₂ |
| [11] | His | Gly | Glu  | Phe  | Thr | Ser | Asp | Leu  | Met  | Phe | Ile | Glu | Phe | Pro | Pro | Pro | Pro | Ser | NH₂ |
| [12] | Tyr | Gly | Glu  | Phe  | Thr | Ser | Asp | Leu  | Met  | Phe | Ile | Glu | Trp | Pro | Pro | Pro | Pro | Ser | NH₂ |
| [13] | His | Gly | Glu  | Phe  | Thr | Ser | Asp | Leu  | Met  | Phe | Ile | Glu | Trp | Pro | Pro | Pro | Pro | Tyr | NH₂ |
| [14] | His | Gly | Asp  | Phe  | Thr | Ser | Asp | Leu  | Met  | Phe | Ile | Glu | Trp | Pro | Pro | Pro | Pro | Ser | NH₂ |
| [15] | His | Gly | Glu  | naph | Thr | Ser | Asp | Leu  | Met  | Phe | Ile | Glu | Trp | Pro | Pro | Pro | Pro | Ser | NH₂ |
| [16] | His | Gly | Glu  | Phe  | Ser | Ser | Asp | Leu  | Met  | Phe | Ile | Glu | Trp | Pro | Pro | Pro | Pro | Ser | NH₂ |
| [17] | His | Gly | Glu  | Phe  | Ser | Thr | Asp | Leu  | Met  | Phe | Ile | Glu | Trp | Pro | Pro | Pro | Pro | Ser | NH₂ |
| [18] | His | Gly | Glu  | Phe  | Thr | Thr | Asp | Leu  | Met  | Phe | Ile | Glu | Trp | Pro | Pro | Pro | Pro | Ser | NH₂ |
| [19] | His | Gly | Glu  | Phe  | Thr | Ser | Glu | Leu  | Met  | Phe | Ile | Glu | Trp | Pro | Pro | Pro | Pro | Ser | NH₂ |
| [20] | His | Gly | Glu  | Phe  | Thr | Ser | Asp | pGly | Met  | Phe | Ile | Glu | Trp | Pro | Pro | Pro | Pro | Ser | NH₂ |
| [21] | His | Gly | Glu  | Phe  | Thr | Ser | Asp | pGly | Leu  | Phe | Ile | Glu | Phe | Pro | Pro | Pro | Pro | Ser | NH₂ |
| [22] | His | Gly | Glu  | Phe  | Thr | Ser | Asp | Leu  | pGly | Phe | Ile | Glu | Trp | Pro | Pro | Pro | Pro | Ser | NH₂ |

FIGURE 9-B

|      |     |     |     |     |     |     |     |     |      |      |     |     |      |      |      |      |     |
|------|-----|-----|-----|-----|-----|-----|-----|-----|------|------|-----|-----|------|------|------|------|-----|
| [23] | His | Gly | Glu | Phe | Thr | Ser | Asp | Leu | pGly | Phe  | Ile | Glu | Phe  | Pro  | Pro  | Pro  | Ser | NH  |
| [24] | His | Gly | Glu | Phe | Thr | Ser | Asp | Leu | Met  | naph | Ile | Glu | Trp  | Pro  | Pro  | Pro  | Ser | NH₂ |
| [25] | His | Gly | Glu | Phe | Thr | Ser | Asp | Leu | Met  | Phe  | Val | Glu | Trp  | Pro  | Pro  | Pro  | Ser | NH₂ |
| [26] | His | Gly | Glu | Phe | Thr | Ser | Asp | Leu | Leu  | Phe  | Val | Glu | Phe  | Pro  | Pro  | Pro  | Ser | NH₂ |
| [27] | His | Gly | Glu | Phe | Thr | Ser | Asp | Leu | Met  | Phe  | tBuG| Glu | Trp  | Pro  | Pro  | Pro  | Ser | NH₂ |
| [28] | His | Gly | Glu | Phe | Thr | Ser | Asp | Leu | Leu  | Phe  | tBuG| Glu | Phe  | Pro  | Pro  | Pro  | Ser | NH₂ |
| [29] | His | Gly | Glu | Phe | Thr | Ser | Asp | Leu | Met  | Phe  | Ile | Asp | Trp  | Pro  | Pro  | Pro  | Ser | NH₂ |
| [30] | His | Gly | Glu | Phe | Thr | Ser | Asp | Leu | Met  | Phe  | Ile | Glu | Phe  | Pro  | Pro  | Pro  | Ser | NH₂ |
| [31] | His | Gly | Glu | Phe | Thr | Ser | Asp | Leu | Met  | Phe  | Ile | Glu | Trp  | tPro | tPro | tPro | Ser | NH₂ |
| [32] | His | Gly | Glu | Phe | Thr | Ser | Asp | Leu | Met  | Phe  | Ile | Glu | Trp  | Pro  | tPro | tPro | Ser | NH₂ |
| [33] | His | Gly | Glu | Phe | Thr | Ser | Asp | Leu | Met  | Phe  | Ile | Glu | Trp  | hPro | hPro | hPro | Ser | NH₂ |
| [34] | His | Gly | Glu | Phe | Thr | Ser | Asp | Leu | Met  | Phe  | Ile | Glu | Trp  | Pro  | hPro | hPro | Ser | NH₂ |
| [35] | His | Gly | Glu | Phe | Thr | Ser | Asp | Leu | Leu  | Phe  | Ile | Glu | Phe  | tPro | tPro | tPro | Ser | NH₂ |
| [36] | His | Gly | Glu | Phe | Thr | Ser | Asp | Leu | Leu  | Phe  | Ile | Glu | Phe  | hPro | hPro | hPro | Ser | NH₂ |
| [37] | His | Gly | Glu | Phe | Thr | Ser | Asp | Leu | Met  | Phe  | Ile | Glu | Trp  | MeAla| MeAla| MeAla| Ser | NH₂ |
| [38] | His | Gly | Glu | Phe | Thr | Ser | Asp | Leu | Met  | Phe  | Ile | Glu | Trp  | Pro  | MeAla| MeAla| Ser | NH  |
| [39] | His | Gly | Glu | Phe | Thr | Ser | Asp | Leu | Leu  | Phe  | Ile | Glu | Phe  | MeAla| MeAla| MeAla| Ser | NH  |

FIGURE 10A

| SEQ ID NO. | |
|---|---|
| 40 | His Gly Glu Gly Thr Phe Thr Ser Asp Leu Ser Lys Gln Met Glu Glu Glu Ala Val Arg Leu Phe Ile Glu Trp Leu Lys Asn-NH$_2$ |
| 41 | His Gly Glu Gly Thr Phe Thr Ser Asp Leu Ser Lys Gln Leu Glu Glu Glu Ala Val Arg Leu Phe Ile Glu Phe Leu Lys Asn-NH$_2$ |
| 42 | His Ala Glu Gly Thr Phe Thr Ser Asp Leu Ser Lys Gln Leu Glu Glu Glu Ala Val Arg Leu Phe Ile Glu Phe Leu Lys Asn-NH$_2$ |
| 43 | His Gly Glu Gly Ala Phe Thr Ser Asp Leu Ser Lys Gln Leu Glu Glu Glu Ala Val Arg Leu Phe Ile Glu Phe Leu Lys Asn-NH$_2$ |
| 44 | His Gly Glu Gly Thr Ala Thr Ser Asp Leu Ser Lys Gln Leu Glu Glu Glu Ala Val Arg Leu Phe Ile Glu Phe Leu Lys Asn-NH$_2$ |
| 45 | His Gly Glu Gly Thr Phe Thr Ala Asp Leu Ser Lys Gln Leu Glu Glu Glu Ala Val Arg Leu Phe Ile Glu Phe Leu Lys Asn-NH$_2$ |
| 46 | His Gly Glu Gly Thr Phe Thr Ser Asp Ala Ser Lys Gln Leu Glu Glu Glu Ala Val Arg Leu Phe Ile Glu Phe Leu Lys Asn-NH$_2$ |
| 47 | His Gly Glu Gly Thr Phe Thr Ser Asp Leu Ala Lys Gln Leu Glu Glu Glu Ala Val Arg Leu Phe Ile Glu Phe Leu Lys Asn-NH$_2$ |
| 48 | His Gly Glu Gly Thr Phe Thr Ser Asp Leu Ser Ala Gln Leu Glu Glu Glu Ala Val Arg Leu Phe Ile Glu Phe Leu Lys Asn-NH$_2$ |

FIGURE 10B

| SEQ ID NO. | |
|---|---|
| 49 | His Gly Glu Gly Thr Phe Thr Ser Asp Leu Ser Lys Ala Leu Glu Glu Glu Ala Val Arg Leu Phe Ile Glu Phe Leu Lys Asn-NH₂ |
| 50 | His Gly Glu Gly Thr Phe Thr Ser Asp Leu Ser Lys Gln Ala Glu Glu Glu Ala Val Arg Leu Phe Ile Glu Phe Leu Lys Asn-NH₂ |
| 51 | His Gly Glu Gly Thr Phe Thr Ser Asp Leu Ser Lys Gln Leu Ala Glu Glu Ala Val Arg Leu Phe Ile Glu Phe Leu Lys Asn-NH₂ |
| 52 | His Gly Glu Gly Thr Phe Thr Ser Asp Leu Ser Lys Gln Leu Glu Ala Glu Ala Val Arg Leu Phe Ile Glu Phe Leu Lys Asn-NH₂ |
| 53 | His Gly Glu Gly Thr Phe Thr Ser Asp Leu Ser Lys Gln Leu Glu Glu Ala Ala Val Arg Leu Phe Ile Glu Phe Leu Lys Asn-NH₂ |
| 54 | His Gly Glu Gly Thr Phe Thr Ser Asp Leu Ser Lys Gln Leu Glu Glu Glu Ala Ala Arg Leu Phe Ile Glu Phe Leu Lys Asn-NH₂ |
| 55 | His Gly Glu Gly Thr Phe Thr Ser Asp Leu Ser Lys Gln Leu Glu Glu Glu Ala Val Ala Leu Phe Ile Glu Phe Leu Lys Asn-NH₂ |
| 56 | His Gly Glu Gly Thr Phe Thr Ser Asp Leu Ser Lys Gln Leu Glu Glu Glu Ala Val Arg Ala Phe Ile Glu Phe Leu Lys Asn-NH₂ |
| 57 | His Gly Glu Gly Thr Phe Thr Ser Asp Leu Ser Lys Gln Leu Glu Glu Glu Ala Val Arg Leu Phe Ile Ala Phe Leu Lys Asn-NH₂ |
| 58 | His Gly Glu Gly Thr Phe Thr Ser Asp Leu Ser Lys Gln Leu Glu Glu Glu Ala Val Arg Leu Phe Ile Glu Ala Leu Lys Asn-NH₂ |
| 59 | His Gly Glu Gly Thr Phe Thr Ser Asp Leu Ser Lys Gln Leu Glu Glu Glu Ala Val Arg Leu Phe Ile Glu Phe Ala Lys Asn-NH₂ |

FIGURE 10C

| SEQ ID NO. | |
|---|---|
| 60 | His Gly Glu Gly Thr Phe Thr Ser Asp Leu Ser Lys Gln Leu Glu Glu Glu Ala Val Arg Leu Phe Ile Glu Phe Leu Ala Asn-NH$_2$ |
| 61 | His Gly Glu Gly Thr Phe Thr Ser Asp Leu Ser Lys Gln Leu Glu Glu Glu Ala Val Arg Leu Phe Ile Glu Phe Leu Lys Ala-NH$_2$ |

SEQUENCE LISTING

<160> NUMBER OF SEQ ID NOS: 79

<210> SEQ ID NO 1
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 1

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 30

```
<212> TYPE: PRT
<213> ORGANISM: Artificial Sequence
<220> FEATURE:
<223> OTHER INFORMATION: Synthetic peptide construct

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic peptide construct

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 5
<211> LENGTH: 28
<212> TYPE: PRT
<213> ORGANISM: Artificial Sequence
<220> FEATURE:
<223> OTHER INFORMATION: Synthetic peptide construct

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 6
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 6

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 7
<211> LENGTH: 28
<212> TYPE: PRT
<213> ORGANISM: Artificial Sequence
<220> FEATURE:
<223> OTHER INFORMATION: Synthetic peptide construct

<400> SEQUENCE: 7

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25
```

<210> SEQ ID NO 8
<211> LENGTH: 28
<212> TYPE: PRT
<213> ORGANISM: Artificial Sequence
<220> FEATURE:
<223> OTHER INFORMATION: Synthetic peptide construct

<400> SEQUENCE: 8

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 9
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 9

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 10
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 10

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence

```
<220> FEATURE:
<223> OTHER INFORMATION: Synthetic peptide construct

<400> SEQUENCE: 12

Tyr Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 13
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Tyr
            35

<210> SEQ ID NO 14
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 14

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 15
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: naphthylalanine

<400> SEQUENCE: 15

His Gly Glu Gly Thr Xaa Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 16
<211> LENGTH: 39
<212> TYPE: PRT
```

```
<213> ORGANISM: Artificial Sequence
<220> FEATURE:
<223> OTHER INFORMATION: Synthetic peptide construct

<400> SEQUENCE: 16

His Gly Glu Gly Thr Phe Ser Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 17

His Gly Glu Gly Thr Phe Ser Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 18

His Gly Glu Gly Thr Phe Thr Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 19

His Gly Glu Gly Thr Phe Thr Ser Glu Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Synthetic peptide construct
```

<220> FEATURE:
<221> NAME/KEY: MOD_RES
<222> LOCATION: (10)..(10)
<223> OTHER INFORMATION: pentylglycine

<400> SEQUENCE: 20

His Gly Glu Gly Thr Phe Thr Ser Asp Xaa Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (10)..(10)
<223> OTHER INFORMATION: pentylglycine

<400> SEQUENCE: 21

His Gly Glu Gly Thr Phe Thr Ser Asp Xaa Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (14)..(14)
<223> OTHER INFORMATION: pentylglycine

<400> SEQUENCE: 22

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (14)..(14)
<223> OTHER INFORMATION: pentylglycine

<400> SEQUENCE: 23

His Gly Glu Gly Thr Phe Thr Ser Asp Leu Ser Lys Gln Xaa Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (22)..(22)
<223> OTHER INFORMATION: naphthylalanine

<400> SEQUENCE: 24

His Gly Glu Gly Thr Phe Thr Ser Asp Leu Ser Lys Gln Met Glu Glu
1               5                   10                  15

Glu Ala Val Arg Leu Xaa Ile Glu Trp Leu Lys Asn Gly Gly Pro Ser
            20                  25                  30

Ser Gly Ala Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 25

His Gly Glu Gly Thr Phe Thr Ser Asp Leu Ser Lys Gln Met Glu Glu
1               5                   10                  15

Glu Ala Val Arg Leu Phe Val Glu Trp Leu Lys Asn Gly Gly Pro Ser
            20                  25                  30

Ser Gly Ala Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 26

His Gly Glu Gly Thr Phe Thr Ser Asp Leu Ser Lys Gln Leu Glu Glu
1               5                   10                  15

Glu Ala Val Arg Leu Phe Val Glu Phe Leu Lys Asn Gly Gly Pro Ser
            20                  25                  30

Ser Gly Ala Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (23)..(23)
<223> OTHER INFORMATION: tert-butylglycine

<400> SEQUENCE: 27

His Gly Glu Gly Thr Phe Thr Ser Asp Leu Ser Lys Gln Met Glu Glu
1               5                   10                  15

Glu Ala Val Arg Leu Phe Xaa Glu Trp Leu Lys Asn Gly Gly Pro Ser
            20                  25                  30

Ser Gly Ala Pro Pro Ser
        35

<210> SEQ ID NO 28
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (23)..(23)
<223> OTHER INFORMATION: tert-butylglycine

<400> SEQUENCE: 28

His Gly Glu Gly Thr Phe Thr Ser Asp Leu Ser Lys Gln Leu Glu Glu
1               5                   10                  15

Glu Ala Val Arg Leu Phe Xaa Glu Phe Leu Lys Asn Gly Gly Pro Ser
            20                  25                  30

Ser Gly Ala Pro Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 29

His Gly Glu Gly Thr Phe Thr Ser Asp Leu Ser Lys Gln Met Glu Glu
1               5                   10                  15

Glu Ala Val Arg Leu Phe Ile Asp Trp Leu Lys Asn Gly Gly Pro Ser
            20                  25                  30

Ser Gly Ala Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 30

His Gly Glu Gly Thr Phe Thr Ser Asp Leu Ser Lys Gln Met Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Synthetic peptide construct

```
<220> FEATURE:
<221> NAME/KEY: MOD_RES
<222> LOCATION: (31)..(31)
<223> OTHER INFORMATION: thioproline
<220> FEATURE:
<221> NAME/KEY: MOD_RES
<222> LOCATION: (36)..(38)
<223> OTHER INFORMATION: thioproline

<400> SEQUENCE: 31

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35

<210> SEQ ID NO 32
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (36)..(38)
<223> OTHER INFORMATION: thioproline

<400> SEQUENCE: 32

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Xaa Xaa Xaa Ser
        35

<210> SEQ ID NO 33
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES
<222> LOCATION: (36)..(38)
<223> OTHER INFORMATION: homoproline

<400> SEQUENCE: 33

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35

<210> SEQ ID NO 34
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
```

```
<222> LOCATION: (36)..(38)
<223> OTHER INFORMATION: homoproline

<400> SEQUENCE: 34

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Xaa Xaa Xaa Ser
        35

<210> SEQ ID NO 35
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (31)..(31)
<223> OTHER INFORMATION: thioproline
<220> FEATURE:
<221> NAME/KEY: MOD_RES
<222> LOCATION: (36)..(38)
<223> OTHER INFORMATION: thioproline

<400> SEQUENCE: 35

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 36
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES
<222> LOCATION: (36)..(38)
<223> OTHER INFORMATION: homoproline

<400> SEQUENCE: 36

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 37
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (31)..(31)
<223> OTHER INFORMATION: N-methylalanine
```

```
<220> FEATURE:
<221> NAME/KEY: MOD_RES
<222> LOCATION: (36)..(38)
<223> OTHER INFORMATION: N-methylalanine

<400> SEQUENCE: 37

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35

<210> SEQ ID NO 38
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (36)..(38)
<223> OTHER INFORMATION: N-methylalanine

<400> SEQUENCE: 38

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Xaa Xaa Xaa Ser
        35

<210> SEQ ID NO 39
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (31)..(31)
<223> OTHER INFORMATION: N-methylalanine
<220> FEATURE:
<221> NAME/KEY: MOD_RES
<222> LOCATION: (36)..(38)
<223> OTHER INFORMATION: N-methylalanine

<400> SEQUENCE: 39

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 40
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION
```

```
<400> SEQUENCE: 40

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 41
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 41

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 42
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 42

His Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 43
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 43

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 44
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION
```

<400> SEQUENCE: 44

His Gly Glu Gly Thr Ala Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 45
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 45

His Gly Glu Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 46
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 46

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 47
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 47

His Gly Glu Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 48
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)

```
<223> OTHER INFORMATION: AMIDATION

<400> SEQUENCE: 48

His Gly Glu Gly Thr Phe Thr Ser Asp Leu Ser Ala Gln Leu Glu Glu
1               5                   10                  15

Glu Ala Val Arg Leu Phe Ile Glu Phe Leu Lys Asn
            20                  25

<210> SEQ ID NO 49
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 49

His Gly Glu Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 50
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 50

His Gly Glu Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 51
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 51

His Gly Glu Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 52
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
```

```
<222> LOCATION: (28)..(28)
<223> OTHER INFORMATION: AMIDATION

<400> SEQUENCE: 52

His Gly Glu Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 53
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 53

His Gly Glu Gly Thr Phe Thr Ser Asp Leu Ser Lys Gln Leu Glu Glu
1               5                   10                  15

Ala Ala Val Arg Leu Phe Ile Glu Phe Leu Lys Asn
            20                  25

<210> SEQ ID NO 54
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 54

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 55
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 55

His Gly Glu Gly Thr Phe Thr Ser Asp Leu Ser Lys Gln Leu Glu Glu
1               5                   10                  15

Glu Ala Val Ala Leu Phe Ile Glu Phe Leu Lys Asn
            20                  25

<210> SEQ ID NO 56
<211> LENGTH: 28
<212> TYPE: PRT
<213> ORGANISM: Artificial Sequence
<220> FEATURE:
<223> OTHER INFORMATION: Synthetic peptide construct
<220> FEATURE:
```

```
<221> NAME/KEY: MOD_RES
<222> LOCATION: (28)..(28)
<223> OTHER INFORMATION: AMIDATION

<400> SEQUENCE: 56

His Gly Glu Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 57
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 57

His Gly Glu Gly Thr Phe Thr Ser Asp Leu Ser Lys Gln Leu Glu Glu
1               5                   10                  15

Glu Ala Val Arg Leu Phe Ile Ala Phe Leu Lys Asn
            20                  25

<210> SEQ ID NO 58
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 58

His Gly Glu Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 59
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 59

His Gly Glu Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 60
<211> LENGTH: 28
<212> TYPE: PRT
<213> ORGANISM: Artificial Sequence
<220> FEATURE:
<223> OTHER INFORMATION: Synthetic peptide construct
```

```
<220> FEATURE:
<221> NAME/KEY: MOD_RES
<222> LOCATION: (28)..(28)
<223> OTHER INFORMATION: AMIDATION

<400> SEQUENCE: 60

His Gly Glu Gly Thr Phe Thr Ser Asp Leu Ser Lys Gln Leu Glu Glu
1               5                   10                  15

Glu Ala Val Arg Leu Phe Ile Glu Phe Leu Ala Asn
            20                  25

<210> SEQ ID NO 61
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (28)..(28)
<223> OTHER INFORMATION: AMIDATION

<400> SEQUENCE: 61

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 62
<211> LENGTH: 39
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Asp or Glu
<220> FEATURE:
<221> NAME/KEY: VARIANT
<222> LOCATION: (6)..(6)
<223> OTHER INFORMATION: Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)
<223> OTHER INFORMATION: Leu, Ile, Val, pentylglycine or Met
<220> FEATURE:
<221> NAME/KEY: VARIANT
<222> LOCATION: (14)..(14)
<223> OTHER INFORMATION: Leu, Ile, pentylglycine, Val or Met
<220> FEATURE:
<221> NAME/KEY: VARIANT
<222> LOCATION: (22)..(22)
```

```
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Glu or Asp
<220> FEATURE:
<221> NAME/KEY: VARIANT
<222> LOCATION: (25)..(25)
<223> OTHER INFORMATION: Trp, Phe, Tyr or naphthylalanine
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglcine, N-alkylpentylglycine or N-alkylalanine
<220> FEATURE:
<221> NAME/KEY: VARIANT
<222> LOCATION: (36)..(38)
<223> OTHER INFORMATION: Pro, homoproline, 3Hyp, 4Hyp, thioproline,
      N-alkylglcine, N-alkylpentylglycine or N-alkylalanine
<220> FEATURE:
<221> NAME/KEY: VARIANT
<222> LOCATION: (39)..(39)
<223> OTHER INFORMATION: Ser, Thr or Tyr

<400> SEQUENCE: 62

Xaa Xaa Xaa Gly Thr Xaa Xaa Xaa Xaa Xaa Ser Lys Gln Xaa Glu Glu
1               5                   10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
        35

<210> SEQ ID NO 63
<211> LENGTH: 30
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
```

```
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
     or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn

<400> SEQUENCE: 63

Xaa Xaa Xaa Gly Xaa Xaa Xaa Xaa Xaa Xaa Xaa Xaa Xaa Xaa Xaa Xaa
1               5                   10                  15
```

Xaa Ala Xaa Xaa Xaa Xaa Xaa Xaa Xaa Xaa Xaa Gly Gly
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:

-continued

```
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine

<400> SEQUENCE: 64

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
```

```
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
```

```
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine

<400> SEQUENCE: 65

Xaa Xaa Xaa Gly Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

<210> SEQ ID NO 66
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
```

```
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine

<400> SEQUENCE: 66

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser

<210> SEQ ID NO 67
<211> LENGTH: 34
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
```

-continued

```
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
```

```
              or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine

<400> SEQUENCE: 67

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly

<210> SEQ ID NO 68
<211> LENGTH: 35
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)
```

-continued

```
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine

<400> SEQUENCE: 68

Xaa Xaa Xaa Gly Xaa Xaa Xaa Xaa Xaa Xaa Xaa Xaa Xaa Xaa Xaa Xaa
```

-continued

```
1               5                   10                  15
Xaa Ala Xaa Xaa Xaa Xaa Xaa Xaa Xaa Xaa Xaa Gly Gly Xaa Ser
        20                  25                  30
Ser Gly Ala
        35

<210> SEQ ID NO 69
<211> LENGTH: 36
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
```

```
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (36)..(36)
<223> OTHER INFORMATION: Pro, homoproline, 3Hyp, 4Hyp, thioproline,
      N-alkylglycine, N-alkylpentylglycine or N-alkylalanine

<400> SEQUENCE: 69

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa
        35

<210> SEQ ID NO 70
<211> LENGTH: 37
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
```

```
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
```

```
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (36)..(37)
<223> OTHER INFORMATION: Pro, homoproline, 3Hyp, 4Hyp, thioproline,
      N-alkylglycine, N-alkylpentylglycine or N-alkylalanine

<400> SEQUENCE: 70

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser Gly Ala Xaa Xaa
        35

<210> SEQ ID NO 71
<211> LENGTH: 38
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
<220> FEATURE:
```

```
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
    or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
    N-alkylglycine, N-alkylpentylglycine or N-alkylalanine
<220> FEATURE:
<221> NAME/KEY: VARIANT
```

```
<222> LOCATION: (36)..(38)
<223> OTHER INFORMATION: Pro, homoproline, 3Hyp, 4Hyp, thioproline,
      N-alkylglycine, N-alkylpentylglycine or N-alkylalanine

<400> SEQUENCE: 71

Xaa Xaa Xaa Gly Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser Gly Ala Xaa Xaa Xaa
            35

<210> SEQ ID NO 72
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg, Tyr, Ala, Norval, Val, or Norleu
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (4)..(4)
<223> OTHER INFORMATION: Ala, Norval, Val, Norleu or Gly
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Ala, Norval, Val, Norleu, Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
```

```
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine

<400> SEQUENCE: 72

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

<210> SEQ ID NO 73
<211> LENGTH: 33
<212> TYPE: PRT
<213> ORGANISM: Artificial Sequence
<220> FEATURE:
<223> OTHER INFORMATION: Synthetic peptide construct
<220> FEATURE:
```

```
<221> NAME/KEY: VARIANT
<222> LOCATION: (1)..(1)
<223> OTHER INFORMATION: His, Arg, Tyr, Ala, Norval, Val, or Norleu
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (4)..(4)
<223> OTHER INFORMATION: Ala, Norval, Val, Norleu or Gly
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Ala, Norval, Val, Norleu, Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
```

```
<220> FEATURE:
<221> NAME/KEY: VARIANT
<222> LOCATION: (22)..(22)
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
     N-alkylglycine, N-alkylpentylglycine or N-alkylalanine
<220> FEATURE:
<221> NAME/KEY: VARIANT
<222> LOCATION: (31)..(31)
<223> OTHER INFORMATION: Pro, homoproline, 3Hyp, 4Hyp, thioproline,
     N-alkylglycine, N-alkylpentylglycine or N-alkylalanine

<400> SEQUENCE: 73

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser

<210> SEQ ID NO 74
<211> LENGTH: 34
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg, Tyr, Ala, Norval, Val, or Norleu
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (4)..(4)
<223> OTHER INFORMATION: Ala, Norval, Val, Norleu or Gly
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
```

```
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Ala, Norval, Val, Norleu, Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
```

```
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine

<400> SEQUENCE: 74

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser Gly

<210> SEQ ID NO 75
<211> LENGTH: 35
<212> TYPE: PRT
<213> ORGANISM: Artificial Sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg, Tyr, Ala, Norval, Val, or Norleu
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (4)..(4)
<223> OTHER INFORMATION: Ala, Norval, Val, Norleu or Gly
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Ala, Norval, Val, Norleu, Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
```

```
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine

<400> SEQUENCE: 75
```

```
Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
        20                  25                  30

Ser Gly Ala
        35

<210> SEQ ID NO 76
<211> LENGTH: 36
<212> TYPE: PRT
<213> ORGANISM: Artificial sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg, Tyr, Ala, Norval, Val, or Norleu
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (4)..(4)
<223> OTHER INFORMATION: Ala, Norval, Val, Norleu or Gly
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Ala, Norval, Val, Norleu, Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
```

```
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (36)..(36)
<223> OTHER INFORMATION: Pro, homoproline, 3Hyp, 4Hyp, thioproline,
      N-alkylglycine, N-alkylpentylglycine or N-alkylalanine

<400> SEQUENCE: 76

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser Gly Ala Xaa
        35

<210> SEQ ID NO 77
<211> LENGTH: 37
<212> TYPE: PRT
<213> ORGANISM: Artificial sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg, Tyr, Ala, Norval, Val, or Norleu
```

```
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (4)..(4)
<223> OTHER INFORMATION: Ala, Norval, Val, Norleu or Gly
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Ala, Norval, Val, Norleu, Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
```

```
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (36)..(37)
<223> OTHER INFORMATION: Pro, homoproline, 3Hyp, 4Hyp, thioproline,
      N-alkylglycine, N-alkylpentylglycine or N-alkylalanine

<400> SEQUENCE: 77

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser Gly Ala Xaa Xaa
        35

<210> SEQ ID NO 78
<211> LENGTH: 38
<212> TYPE: PRT
<213> ORGANISM: Artificial sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg, Tyr, Ala, Norval, Val, or Norleu
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (4)..(4)
<223> OTHER INFORMATION: Ala, Norval, Val, Norleu or Gly
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
```

```
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Ala, Norval, Val, Norleu, Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
```

```
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (36)..(38)
<223> OTHER INFORMATION: Pro, homoproline, 3Hyp, 4Hyp, thioproline,
      N-alkylglycine, N-alkylpentylglycine or N-alkylalanine

<400> SEQUENCE: 78

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa
        35

<210> SEQ ID NO 79
<211> LENGTH: 39
<212> TYPE: PRT
<213> ORGANISM: Artificial sequence
<220> FEATURE:
<223> OTHER INFORMATION: Synthetic peptide construct
<220> FEATURE:
<221> NAME/KEY: VARIANT
<222> LOCATION: (1)..(1)
<223> OTHER INFORMATION: His, Arg, Tyr, Ala, Norval, Val, or Norleu
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (4)..(4)
<223> OTHER INFORMATION: Ala, Norval, Val, Norleu or Gly
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Ala, Norval, Val, Norleu, Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
```

```
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(15)
<223> OTHER INFORMATION: Ala or Glu
<220> FEATURE:
<221> NAME/KEY: VARIANT
<222> LOCATION: (16)..(16)
<223> OTHER INFORMATION: Ala or Glu
<220> FEATURE:
<221> NAME/KEY: VARIANT
<222> LOCATION: (17)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, tert-butylglycine
      or Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (36)..(38)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (39)..(39)
<223> OTHER INFORMATION: Ser, Thr, Lys or Ala
```

```
<400> SEQUENCE: 79

Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser Gly Ala Xaa Xaa Xaa Xaa
            35
```

USE OF EXENDIN AND ANALOGS THEREOF TO DELAY OR PREVENT CARDIAC REMODELING

CROSS REFERENCE TO RELATED APPLICATIONS

This is a National Stage application of International Application No. PCT/US2006/013949, filed Apr. 11, 2006, now published as WO2006/110887, which claims the benefit of U.S. Provisional Application No. 60/669,876, filed Apr. 11, 2005, each of which is hereby incorporated by reference in their entireties, including all tables, figures, and claims.

INCORPORATION-BY-REFERENCE OF MATERIAL SUBMITTED ON COMPACT DISCS

The sequence listing in the present application is being submitted electronically on compact disc in a file created on May 13, 2008, the contents of which are hereby incorporated by reference.

TECHNICAL FIELD

Provided herein are uses of compounds referred to as cardioprotective incretin compounds (CICs) such as GLP-1, exendin, and agonists and analogs thereof, for the treatment of cardiac diseases or disorders, and more particularly to ameliorate, attenuate, delay the onset of, or prevent cardiac remodeling.

BACKGROUND

Cardiac remodeling is a complex process that results in structural and functional changes in one or more chambers in the heart, especially the ventricles. Macroscopically, such changes lead to an increase in end-diastolic and end-systolic volume, an alteration in the shape of the heart from ellipsoid to a more spherical form, and cardiac hypertrophy, most notably an increase in the left ventricular mass (LV mass). Remodeling can occur essentially after any insult to the myocardium and is a progressive and self-perpetuating process that involves a period of myocellular hypertrophy, followed by an absolute reduction in cell number. Following an insult, genomic changes resulting from the insult lead to subsequent molecular, cellular and interstitial changes, leading to the structural alterations discussed above, and is manifested clinically as changes in the size and function of the heart. As such, cardiac remodeling is a significant contributor to cardiac diseases, such as the development and progression of congestive heart failure. Cardiac remodeling can also lead to arrhythmias and sudden death, such as those caused by cardiac dysrhythmia.

Congestive heart failure is one of the most significant causes of morbidity and mortality in developed countries. It occurs as a late manifestation in diverse cardiovascular diseases characterized by loss of contractile mass and/or by volume or pressure overload (Fortuno, *Hypertension* 38: 1406-1412 (2001)). Numerous studies have proposed that cardiac remodeling is a major determinant of the clinical course of CHF, irrespective of its etiology (Fedak, *Cardiovascular Pathology* 14:1-11 (2005)). Cardiac remodeling is thus an attractive target for the treatment of congestive heart failure. As such, agents that act to prevent or decrease cardiac remodeling are desired. Indeed, the literature has identified a need for molecules that can attenuate cardiac remodeling (Fortuno, *Hypertension* 38:1406-1412 (2001)). Literature reports indicate that attenuating ventricular remodeling also improves survival after myocardial insult, while treatments which worsen remodeling have been associated with poorer outcomes even when they improve systolic function (See, Somasundaram, *Med. Clin. N. Am.*, 88: 1193-1207 (2004)).

Literature reports indicate that GLP-1 released from gut endocrine L cells is a regulator of the phosphoinositide 3-kinase in pancreatic β-cells (Buteau, *Diabetologica* 42:856-864 (1999)). This kinase has been associated with myocardial protection in ischemic/reperfusion injury and myocardial preconditioning settings (See e.g., Bose, et al., *Diabetes* 54: 146-151 (2005)). More particularly, GLP-1 has been used to prevent myocardial infarction in isolated and intact rat heart (See id). According to the literature, GLP-1 released from the pancreas acts by activating a GLP-1 receptor, one such receptor has been identified as a 463-amino acid member of the G protein-coupled receptor superfamily (Drucker, *Diabetes* 47: 159-169 (1998)). It has been reported that a GLP-1 receptor in cardiac myocytes is structurally identical to the pancreatic islet receptor (See id.).

GLP-1 has been described in the treatment of certain cardiac conditions in U.S. Pat. No. 6,277,819, WO 99/40788, WO 01/89554, WO 03/084563, and WO/056313. However, until now, the use of cardioprotective incretin compounds (CICs), such as GLP-1, exendin, agonists and analogs thereof, to ameliorate, attenuate, delay, or prevent cardiac remodeling has not yet been described. Previous treatments of cardiac remodeling have included pharmaceutical, surgical and catheter-based interventions. Despite the ongoing research and development of treatments for cardiac remodeling, there is still a tremendous need for improved and alternative treatments.

SUMMARY

The present methods relates generally to the use of a CIC, to ameliorate, attenuate, delay, or prevent cardiac remodeling following an insult to the heart. Examples of an insult can be those caused by hypertension, dilated cardiomyopathy, or coronary disease, such as an infarct. Insults to the heart can also occur as a result of infections, inflammation, surgery, and a genetic predisposition. An "CIC" as used herein refers to any compound that 1) can mimic an effect of an incretin hormone (incretin mimetic) or can bind to a GLP-1 receptor; and 2) that has an ability to a) ameliorate (improve) at least one cardiac parameter such as left ventricular diastolic function, E wave to A wave ratio, left ventricular end diastolic pressure, cardiac output, cardiac contractility, left ventricular mass, left ventricular mass to body weight ratio, left ventricular volume, left atrial volume, left ventricular end diastolic dimension or systolic dimension, infarct size, exercise capacity, exercise efficiency, or any measure of cardiac systolic and/or diastolic function; or b) attenuate, delay, or prevent at least one deleterious effect on any of the cardiac parameters described in a) or enlargement of a heart chamber. These cardiac properties can be measured by assays known in the art and the assays herein described. Exemplary CICs include GLP-1, exendins, agonists and analogs thereof.

In another aspect, provided herein are methods for using CIC for the treatment of conditions associated with cardiac remodeling. In another aspect, provided herein are methods of delaying or preventing conditions that result from cardiac remodeling. Conditions associated with or resulting from cardiac remodeling that can benefit from the methods provided herein include left ventricular hypertrophy, coronary artery disease, essential hypertension, acute hypertensive emergency, cardiomyopathy, heart insufficiency, exercise tolerance, chronic heart failure, arrhythmia, cardiac dysrhythmia, sudden death, syncopy, atherosclerosis, mild chronic heart failure, angina pectoris, cardiac bypass reocclusion, intermittent claudication, diastolic dysfunction, and/or systolic dysfunction. For example, it is contemplated that a CIC compound has an ability to prevent, attenuate or delay an increase in heart chamber dimension or wall thickness, increase E/A ratio after myocardial infarction; decrease infarct size; increase exercise capacity; increase exercise efficiency; and/or normalize cardiac output after myocardial infarction.

In one embodiment, a method for preventing, delaying, attenuating, or ameliorating cardiac remodeling in a subject in need thereof is provided. The method comprises administering to the subject an amount of a CIC effective to prevent or ameliorate cardiac remodeling.

In another embodiment, a method for improving cardiac contractility in a subject in need thereof is provided. The method generally comprises administering to a subject an amount of a CIC effective to improve cardiac contractility in the subject.

In yet another embodiment, a method for reducing or preventing atrial remodeling in a subject in need thereof is provided. In yet another embodiment, a method for reducing or preventing ventricular remodeling in a subject in need thereof is provided. The methods generally comprise administering to the subject an amount of a CIC effective to reduce or prevent atrial or ventricular remodeling in the subject.

In yet another embodiment, a method for the amelioration, attenuation, treatment or prevention of a condition associated with cardiac remodeling in a subject in need thereof is provided. The method generally comprises administering to a subject an amount of a CIC effective to prevent or ameliorate cardiac remodeling, wherein the condition associated with cardiac remodeling is thereby improved.

Further provided herein is the use of a CIC comprising an amount of CIC sufficient to mediate the effects or treat the diseases or disorders disclosed herein. Also provided is the use of at least one CIC to manufacture a medicament to mediate the effects or treat the diseases or disorders disclosed herein.

CERTAIN EMBODIMENTS

Embodiment 1

A method for preventing or ameliorating cardiac remodeling in a subject, said method comprising: administering an amount of a CIC effective to prevent or ameliorate cardiac remodeling to a subject in need or desirous thereof.

Embodiment 2

The method according to Embodiment 1, wherein said subject has experienced or is experiencing a myocardial insult.

Embodiment 3

The method according to Embodiment 2, wherein said myocardial insult is the result of a condition selected from the group consisting of cardiac valve disease, a myocardial infarction, cardiomyopathy, hypertension, volume overload, cor-pulmonale and pulmonary hypertension.

Embodiment 4

The method according to Embodiments 1-3, wherein said subject is also suffering from diabetes.

Embodiment 5

The method according to any one of Embodiments 1-4, wherein said CIC is acutely administered to said subject.

Embodiment 6

The method according to any one of Embodiments 1-4, wherein said CIC is chronically administered to said subject.

Embodiment 7

The method according to any one of Embodiments 1-6, wherein said CIC is GLP-1.

Embodiment 8

The method according to any one of Embodiments 1-6, wherein said CIC is a GLP-1 analog with GLP-1 activity.

Embodiment 9

The method according to any one of Embodiments 1-6, wherein said CIC is a GLP-1 receptor agonist.

Embodiment 10

The method according to any one of Embodiments 1-6, wherein said CIC is an exendin.

Embodiment 11

The method according to Embodiment 10, wherein said CIC is exendin-4.

Embodiment 12

The method according to any one of Embodiments 1-11, wherein said CIC is parenterally administered to said subject.

Embodiment 13

A method for preventing or reducing atrial or ventricular remodeling in a subject in need thereof, said method comprising: administering an amount of a CIC effective to prevent or reduce atrial or ventricular remodeling to a subject in need or desirous thereof.

Embodiment 14

A method for reducing atrial or ventricular remodeling in a subject, said method comprising: administering an amount of a CIC effective to reduce atrial or ventricular remodeling to a subject in need or desirous thereof.

Embodiment 15

A method for the treatment or prevention of a condition associated with cardiac remodeling in a subject, said method comprising: administering an amount of a CIC effective to prevent cardiac remodeling to a subject in need thereof, wherein said condition associated with cardiac remodeling is thereby improved.

Embodiment 16

The method according to any of Embodiments 13, 14 or 15, wherein said subject has experienced or is experiencing a myocardial insult.

Embodiment 17

The method according to Embodiment 16, wherein said myocardial insult is the result of a condition selected from the group consisting of cardiac valve disease, a myocardial infarction, cardiomyopathy, hypertension, volume overload, cor-pulmonale and pulmonary hypertension.

Embodiment 18

The method according to Embodiments 13-17 wherein said subject is also suffering from diabetes.

Embodiment 19

The method according to any one of Embodiments 13-18, wherein said CIC is acutely administered to said subject.

Embodiment 20

The method according to any one of Embodiments 13-18, wherein said CIC is chronically administered to said subject.

Embodiment 21

The method according to any one of Embodiments 13-18, wherein said CIC is GLP-1.

Embodiment 22

The method according to any one of Embodiments 13-18, wherein said CIC is a GLP-1 analog with GLP-1 activity.

Embodiment 23

The method according to any one of Embodiments 13-18, wherein said CIC is a GLP-1 receptor agonist.

Embodiment 24

The method according to any one of Embodiments 13-18, wherein said CIC is an exendin.

Embodiment 25

The method according to Embodiment 24, wherein said CIC is exendin-4.

Embodiment 26

The method according to any one of Embodiments 13-26, wherein said CIC is parenterally administered to said subject.

BRIEF DESCRIPTION OF THE DRAWINGS

FIG. 4A: LV Systolic Volume (mL) as a function of time after heart failure. FIG. 4B: LV Diastolic Volume (mL) as a function of time after heart failure. FIG. 4C: Left Atrial Volume (mL) as a function of time after heart failure. Legend: Control (solid triangle, tip up); GLPL (open triangle); GLPH (solid triangle, tip down); AC3174L (solid circle); AC3174H (open circle), as described herein.

FIG. 6A: Histogram of Exercise Capacity (Kg-meter) as a function of treatment. FIG. 6B: Histogram of Peak Oxygen Uptake as a function of treatment. Treatment in order (left to right): sham, control, GLPL, GLPH, 3174L, 3174H, as described herein.

FIG. 8A: Histogram of Peak Plasma Lactate level as a function of treatment. FIG. 8B: Histogram of Exercise Capacity/Lactate ratio as a function of treatment. Treatment in order (left to right): sham, control, GLPL, GLPH, 3174L, 3174H, as described herein.

FIGS. 9A and 9B illustrates certain CICs useful in the methods provided herein.

FIGS. 10A-10C illustrate additional CICs useful in the methods provided herein. FIG. 10A: SEQ ID NOs:40-48. FIG. 10B: SEQ ID NOs: 49-59. FIG. 10C: SEQ ID NOs:60-61.

DETAILED DESCRIPTION

Figure 1:
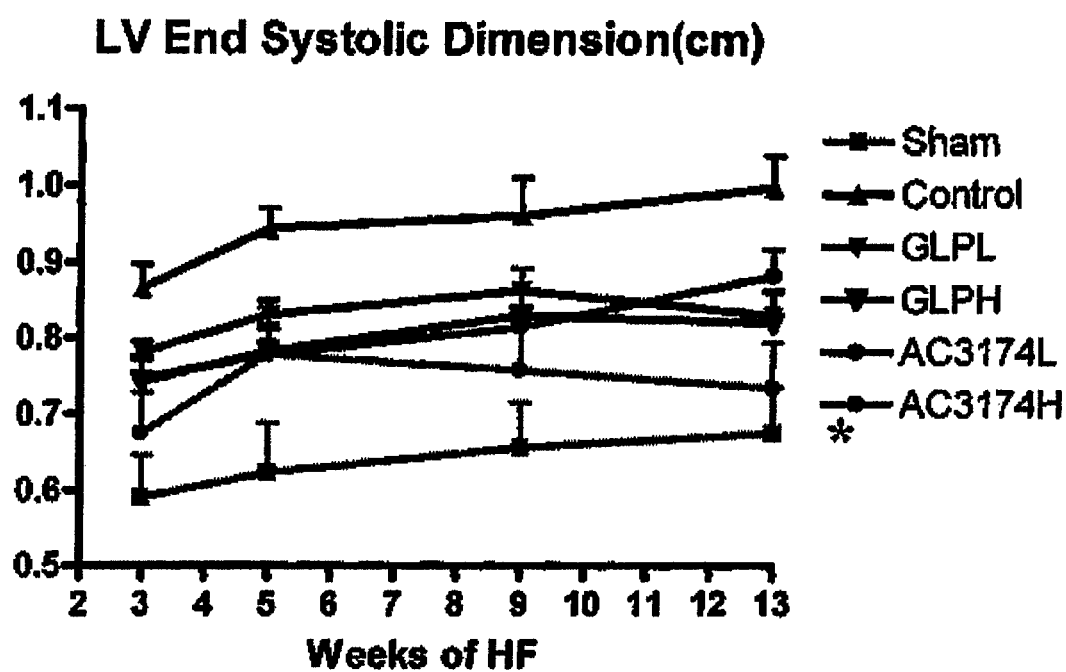
FIG. 1 demonstrates the effect of CICs on the enlargement of the heart chamber using LV end systolic dimension analysis.

Provided herein are methods for preventing, delaying the onset of, attenuating, or ameliorating cardiac remodeling. In general, cardiac remodeling refers to a restructuring and reshaping of any of the cardiac chambers of the heart. In one embodiment, cardiac remodeling refers to the restructuring and reshaping of the ventricles. As described above and without intending to be limited by theory, cardiac remodeling can be described as genomic changes following an insult to the myocardium, with subsequent molecular, cellular and interstitial changes, leading to the restructuring and reshaping of the cardiac chambers. Such restructuring and reshaping can be manifested clinically as changes in size, shape, and function of the heart.

Cardiac remodeling can occur in response to any stimulus or combination of stimuli to the myocardium. In one embodiment, cardiac remodeling is the result of a myocardial insult. By way of non-limiting examples, cardiac remodeling can occur in response to myocardial insults resulting from myocardial infarction, hypertension, volume overload (e.g. from aortic regurgitation), infection, inflammation, diabetes, viral cardiomyopathy, and idiopathic cardiomyopathy.

In one aspect, cardiac remodeling is prevented, delayed, attenuated, or ameliorated by the administration of a CIC. In the context of the present methods, prevention or amelioration of cardiac remodeling can include a reduction of cardiac remodeling by any amount. In an embodiment, prevention or amelioration of cardiac remodeling is accompanied by a reduced risk of congestive heart failure (CHF).

In an embodiment, cardiac remodeling is ameliorated or reduced to an amount that is less than about 1%, 2%, 5%, 10%, 20%, 30%, 40%, 50%, 60%, 70%, 80%, or 90% of the amount of cardiac remodeling in the absence of administering a CIC. In another embodiment, cardiac remodeling can be slightly reduced, moderately reduced, substantially reduced, or substantially eliminated, as compared to the occurrence of cardiac remodeling in the absence of administering a CIC. As used herein, a slight reduction of cardiac remodeling refers to cardiac remodeling that is decreased by about 25% or less as compared with cardiac remodeling in the absence of administering a CIC. A moderate reduction in cardiac remodeling refers to cardiac remodeling that decreased by about 50% or less as compared with cardiac remodeling in the absence of administering an CIC. A substantial reduction in cardiac remodeling refers to cardiac remodeling that decreased by about 80% or less as compared with cardiac remodeling in the absence of administering a CIC. A substantial elimination of cardiac remodeling refers to cardiac remodeling that is decreased by about 80% or more as compared with cardiac remodeling in the absence of administering a CIC.

In order to assess the degree to which cardiac remodeling is prevented, ameliorated, attenuated or delayed, any means available to the skilled worker in the art can be employed. For example, cardiac remodeling can be assessed by analyses including but not limited to histological examination of the heart, LV mass, or during the life by measurement of chamber dimensions and wall thickness and motion, for example by echocardiography or quantifying the Left Ventricle (LV) diastolic function using the peak velocity ratio of the E wave and A wave (E/A ratio).

In an embodiment, the methods provided herein contemplate administering to a sample or subject an amount of one or more CICs effective in preventing, delaying, attenuating or ameliorating cardiac remodeling. A sample includes any material that contains one or more cardiac myocytes. For example, a sample can include one or more cells, tissues, or cultures. An exemplary sample is a human heart. A subject can be any organism that comprises one or more cardiac cells. The cardiac cells can be native to the organism, or alternatively, the cells can be introduced, such as for example by transplantation. Exemplary non-limiting subjects include organisms such as pigs, mice, rats, dogs, cats, chickens, sheep, goats, cattle, and humans. A preferred subject is a human.

In an embodiment, samples and subjects that may be benefited by administration of a CIC to prevent, ameliorate, attenuate, or delay cardiac remodeling can be ascertained by the artisan in light of conditions and risk factors related to the sample or subject. In one embodiment, subjects may be in need of prevention, amelioration, attenuation, or delay of cardiac remodeling. In another embodiment, the subject may be desirous of preventing, ameliorating, attenuating or delaying cardiac remodeling. One risk factor may be a genetic predisposition for a heart to undergo cardiac remodeling. Exemplary samples and subjects of the present methods provided herein include those which have experienced, are experiencing or are at risk to experience a condition associated with cardiac remodeling. A condition associated with cardiac remodeling can be any condition or disorder in which cardiac remodeling is known to occur or thought to be a risk. Conditions associated with cardiac remodeling include, for example, myocardial infarction, inflammation, ischemia/reperfusion, oxidative stress, cor pulmonale, advanced glycation endproducts, abnormal cardiac wall tension, sympathetic stimulation, myocarditis, hypertension, viral cardiomyopathy, idiopathic cardiomyopathy, heart transplantation, and surgical procedures of the heart.

In accordance with the methods described herein, a CIC may be administered in any manner known in the art that renders a CIC biologically available to the subject or sample in an effective amount. For example, the CIC may be administered to a subject via any central or peripheral route known in the art including, but not limited to: oral, parenteral, transdermal, transmucosal, or pulmonary routes. A particular methods employs parenteral administration. Exemplary routes of administration include oral, ocular, rectal, buccal, topical, nasal, ophthalmic, subcutaneous, intramuscular, intraveneous, intracerebral, transdermal, and pulmonary. One exemplary route of administration is subcutaneous. Further, the CIC can be administered to a sample via pouring, pipetting, immersing, injecting, infusing, perfusing, or any other means known in the art. Determination of the appropriate administration method is usually made upon consideration of the condition (e.g., disease or disorder) to be treated, the stage of the condition (e.g., disease or disorder), the comfort of the subject, and other factors known to those of skill in the art.

Administration by the methods provided herein can be intermittent or continuous, both on an acute and/or chronic basis. One mode of administration of a CIC is continuous. Continuous intravenous or subcutaneous infusion, and continuous transcutaneous infusion are exemplary embodiments of administration for use in the methods provided herein. Subcutaneous infusions, both acute and chronic, represent embodiments of continuous administration. Another exemplary mode of administration is intermittent subcutaneous injection. In another exemplary mode of administration, the CIC is formulated for extended or sustained release. Exemplary formulations are reported for example in WO2005000222, US20040228833, US20040208929, US 20050031549, and US20050002927, the entireties of which are incorporated herein by reference In one embodiment, administration of a CIC to prevent or delay cardiac remodeling can be a prophylactic treatment, beginning concurrently with the diagnosis of conditions (e.g., disease or disorder) which places a subject at risk of cardiac remodeling, such as, for example, upon a diagnosis of diabetes or pulmonary hypertension. In the alternative, administration of a CIC to prevent, ameliorate, attenuate, or delay cardiac remodeling can occur subsequent to occurrence of an insult or symptoms associated with cardiac remodeling. In certain embodiments, for example when the insult may be a myocardial infarct, treatment may not begin until 3 days (72 hours) after the insult or the appearance of symptoms associated with the insult. Accordingly, methods provided herein include administration of a CIC after 3 (72 hours), 4, 5, 6, 7, 8, 9, 10, 11, 12, 13, or 14 days after a myocardial insult or the symptoms thereof. In certain embodiments, methods can comprise administering a CIC for more than 1 week, 2 weeks, 3 weeks, 1 month, 2 months, 3 months, 6 months, 1 year, or 2 years after the start of the CIC treatment. In certain embodiments, treatment with a CIC may continue for the duration of the condition, or for the life of the subject.

The term "effective amount" refers to an amount of a pharmaceutical agent used to treat, ameliorate, prevent, or eliminate the identified condition (e.g., disease or disorder), or to exhibit a detectable therapeutic or preventative effect. The effect can be detected by, for example, chemical markers, antigen levels, cardiac function, physical measurements of the heart, or time to a measurable event, such as morbidity or mortality. Therapeutic effects include preventing or reducing the risk of or lessening the severity of congestive heart failure (CHF). Therapeutic effects also include an improvement in cardiac contractility. Further therapeutic effects include reduction in physical symptoms of a subject, such as, for example, an increased capacity or efficiency for physical activity (exercise capacity or efficiency) prior to breathlessness. The precise effective amount for a subject will depend upon the subject's body weight, size, and health; the nature and extent of the condition; and the therapeutic or combination of therapeutics selected for administration. Effective amounts for a given situation can be determined by routine experimentation that is within the skill and judgment of the clinician.

For any CIC, the effective amount can be estimated initially either in cell culture assays, or in animal models, such as rat or mouse models. An animal model may also be used to determine the appropriate concentration range and route of administration. Such information can then be used to determine useful doses and routes for administration in humans.

Efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies may be used in formulating a range of doses for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to CIC employed in the methods provided herein indicate an initial target plasma concentration ranging from about 5 pM to about 400 pM, from about 20 pM to about 200 pM, from about 80 pM to about 100 pM. To achieve such plasma concentrations in the methods provided herein, a CIC may be administered at doses that vary from about 0.25 pmol/kg/min to about 10 nmol/kg/min, about 0.45 pmol/kg/min to about 4.5 nmol/kg/min, depending upon the route of administration. Guidance as to particular dosages and methods of delivery is generally available to practitioners in the art and is provided herein.

In general, for continuous subcutaneous infusion, the dose will be in the range of about 0.2 pmol/kg/min to about 35 pmol/kg/min, or from about 0.3 pmol/kg/min to about 30 pmol/kg/min, or from about 0.45 pmol/kg/min to about 25 pmol/kg/min. For acute subcutaneous infusion, the dose will generally be in the range of about 2.5 pmol/kg/min to about 7 nmol/kg/min, or from about 3.5 pmol/kg/min to about 6 pmol/kg/min, or from about 5 pmol/kg/min to about 4.5 nmol/kg/min. Exemplary treatment regimens include, but are not limited to, administration via injection to achieve a dose of from about 0.1 µg/kg to about 0.5 µg/kg or from about 0.005 µg/kg to about 0.2 µg/kg of the CIC. Other exemplary treatment regimens include, but are not limited to, administration via injection to achieve a dose of from about 1 µg/day to about 1 mg/day or from about 500 µg/day to about 12,000 µg/day of the CIC in a single or divided dose.

Still other exemplary treatment regimens include, but are not limited to, pulmonary administration to achieve a dose from about 100 µg/day to about 12,000 µg/day of the CIC in a single or divided dose; nasal administration to achieve a dose from about 10 µg/day to about 12,000 µg/day of the CIC in a single or divided dose; and buccal administration to achieve a dose from about 100 µg/day to about 12,000 µg/day of the CIC in a single or divided dose.

The exact dosage will be determined by the practitioner, in light of factors related to the subject that requires treatment.

As mentioned above, the CIC may be administered as a result of an acute event or a chronic condition. Whether it is an acute event or a chronic condition, methods provided herein include chronic treatment with a CIC. Thus, length of chronic treatment may include the time when the event has passed and the subject is considered to have recovered from the acute event or recovered from the chronic condition.

Chronic administration of or treatment with the CIC for the prevention, attenuation, delay, or amelioration of cardiac remodeling may be warranted where no particular transient event or transient condition associated with cardiac remodeling is identified. Chronic administration includes administration of a CIC over an indefinite period of time on the basis of a general predisposition to cardiac remodeling or on the basis of a predisposing condition that is non-transient (e.g., a condition that is non-transient may be unidentified or unamenable to elimination, such as diabetes). A CIC may be administered chronically in the methods provided herein in order to prevent cardiac remodeling in a subject who exhibits congestive heart failure, regardless of etiology. Chronic administration of a CIC for the prevention or amelioration of cardiac remodeling may also be implicated in diabetics at risk for congestive heart failure. A CIC may also be administered on a chronic basis in order to preserve a transplanted organ in individuals who have received a heart transplant. When a CIC is administered chronically, administration may continue for any length of time. However, chronic administration often occurs for an extended period of time. For example, in an exemplary embodiment, chronic administration continues for 6 months, 1 year, 2 years or longer.

In another embodiment, the methods disclosed herein lead to improved cardiac contractility. Improving cardiac contractility may include the ability of cardiac myocytes to contract. In order to evaluate the improvement of cardiac contractility, any mode of assessment may be used. For example, clinical observation, such as an increase in cardiac output or a decrease in cardiac rate or both, may lead to a determination of increased cardiac contractility. Alternatively, in vivo, an increased contractility of the heart may be assessed by a determination of an increased fractional shortening of the left ventricle. Fractional shortening of the left ventricle may be observed by any available means such as echocardiograph.

In evaluating increased cardiac contractility, the increase in fractional shortening of the left ventricle may be an increase of any amount as compared with the fractional shortening before administration of a CIC. For example, the increase in shortening may be about 10%, 20%, 30%, 40%, 50%, 60%, 70%, 80%, 90%, 100%, 150%, 200% or more than about 200%.

In yet another aspect, a method for reducing or preventing atrial remodeling by the administration of a CIC is provided. Reduction or prevention of atrial remodeling may be evaluated as compared to atrial remodeling before administration of a CIC. The therapeutic effects of such reduction or prevention of atrial remodeling includes a reduction in atrial fibrillation. In still another aspect, a method for reducing or preventing ventricular remodeling by the administration of a CIC is provided. Reduction or prevention of ventricular remodeling may be evaluated as compared to ventricular remodeling before administration of a CIC.

In a further aspect, prophylactic and therapeutic methods are provided. Treatment on an acute or chronic basis is contemplated. In addition, treatment on an acute basis may be extended to chronic treatment, if so indicated. Chronic treatment is contemplated as being longer than 2 weeks. In certain embodiments, chronic treatment may be longer than 1 month, 3 months, 6 months, 1 year, 2 years, 5 years, or over a life. In one aspect, provided herein is a method for the treatment or prevention of a condition associated with cardiac remodeling in a subject in need thereof. The method generally comprises administering to the subject an amount of a CIC effective to prevent or ameliorate cardiac remodeling, wherein the condition associated with remodeling is thereby improved, prevented or delayed. As described herein, administration of an CIC may be done in any manner and with any CIC such as GLP-1, exendin, and their agonists.

In yet another embodiment, the methods provided herein further comprise the identification of a subject in need of treatment. Any effective criteria may be used to determine that a subject may benefit from administration of a CIC. Methods for the diagnosis of heart disease and diabetes, for example, as well as procedures for the identification of individuals at risk for development of these conditions, are well known to those in the art. Such procedures may include clinical tests, physical examination, personal interviews and assessment of family history.

In the context of the present methods, a CIC includes any molecule that 1) can mimic an effect of an incretin hormone (incretin mimetic) or can bind to a GLP-1 receptor; and 2) that has an ability to ameliorate (improve) at least one of the following cardiac parameters: left ventricular diastolic function, E wave to A wave ratio, left ventricular end diastolic pressure, cardiac output, cardiac contractility, left ventricular mass, left ventricular mass to body weight ratio, left ventricular volume, left atrial volume, left ventricular end diastolic dimension or systolic dimension, infarct size, exercise capacity, exercise efficiency or any measure of cardiac systolic and/or diastolic function; or attenuate, delay, or prevent enlargement of a heart chamber or a deleterious effect on one of the above cardiac parameters. The cardiac parameters can be monitored by assays known in the art and those herein described. An example of an incretin hormone is GLP-1. An example of an effect of an incretin is its glucose-stimulated insulin secretion or ability to improve glucose homeostasis. Examples of incretin mimetics (and CICs) include GLP-1, exendins, and agonists thereof.

An agonist of GLP-1 or exendin can be any molecule that has at least one activity or function of GLP-1 or exendin, respectively, as known in the art or herein described. An agonist of GLP-1 or exendin can be any molecule that can bind to a GLP-1 receptor. An agonist may be a peptide or non-peptide, such as a small molecule.

Accordingly, in one embodiment, a CIC may be identified by its ability to bind or activate a GLP-1 receptor (e.g., a GLP-1 receptor agonist). A GLP-1 receptor is a cell-surface protein. In this regard, a CIC includes any molecule that binds to or activates a GLP-1 receptor.

Generally, GLP-1 receptor agonists can include peptides and small molecules, as known in the art. Exemplary GLP-1 receptor agonists have been described, such as those in Drucker, *Endocrinology* 144(12):5145-5148 (2003); EP 0708179; Hjorth et al., *J. Biol. Chem.* 269(48): 30121-30124 (1994); Siegel et al., Amer. Diabetes Assoc. 57$^{th}$ Scientific Sessions, Boston (1997); Hareter et al., Amer. Diabetes Assoc. 57$^{th}$ Scientific Sessions, Boston (1997); Adelhorst et al., *J. Biol. Chem.* 269(9): 6275-6278 (1994); Deacon et al., 16$^{th}$ International Diabetes Federation Congress Abstracts, *Diabetologia Supplement* (1997); Irwin et al., *Proc. Natl. Acad. Sci. USA.* 94: 7915-7920 (1997); Mosjov, *Int. J Peptide Protein Res.* 40: 333-343 (1992); Göke et al., *Diabetic Medicine* 13: 854-860 (1996). Publications also disclose Black Widow GLP-1 and Ser$^2$ GLP-1. See Holz et al., *Comparative Biochemistry and Physiology, Part B* 121: 177-184 (1998) and Ritzel et al., "A synthetic glucagon-like peptide-1 analog with improved plasma stability," *J. Endocrinol.* 159(1): 93-102 (1998).

In order to determine the ability of a molecule to bind or activate a GLP-1 receptor, any available means can be used. In one embodiment, GLP-1 receptor binding or activation can be determined in either an in vitro or an in vivo model. In one embodiment, receptor-binding activity screening procedures may be used, such as for example, providing any cells that express a GLP-1 receptor on the surface and measuring specific binding using radioimmunoassay methods. The cells expressing a GLP-1 receptor can be naturally occurring or genetically modified. The cells expressing a GLP-1 receptor may be cardiac myocyte cells. In one aspect, GLP-1 receptor binding or activation can be determined with the aid of combinatorial chemistry libraries and high throughput screening techniques, as is known in the art.

In one embodiment, CICs include exendin molecules, including exendin-1, exendin-2, exendin-3, exendin-4, and analogs thereof. Particular exendin molecules include exendin-3 and exendin-4, and analogs thereof. Such exendin molecules are generally known in the art and available to the skilled artisan.

By way of background, exendins are peptides that are found in the saliva of the Gila-monster, a lizard endogenous to Arizona, and the Mexican Beaded Lizard. Exendin-3 is present in the saliva of *Heloderma horridum*, and exendin-4 is present in the saliva of *Heloderma suspectum* (Eng, J., et al., *J. Biol. Chem.*, 265:20259-62 (1990); Eng., J., et al., *J. Biol. Chem.*, 267:7402-05 (1992)). The exendins have some sequence similarity to several members of the glucagon-like peptide family, with the highest identity, 53%, being to GLP-1 (Goke, et al., *J. Biol. Chem.*, 268:19650-55 (1993)).

Exendin-4 is a potent agonist at GLP-1 receptors on insulin-secreting TC1 cells, at dispersed acinar cells from guinea pig pancreas, and at parietal cells from stomach; the peptide also stimulates somatostatin release and inhibits gastrin release in isolated stomachs (Goke, et al., *J. Biol. Chem.*, 268:19650-55 (1993); Schepp, et al., *Eur. J. Pharmacol.*, 69:183-91 (1994); Eissele, et al., *Life Sci.*, 55:629-34 (1994)). Exendin-3 and exendin-4 were found to be GLP-1 agonists in stimulating cAMP production in, and amylase release from, pancreatic acinar cells (Malhotra, R., et al., *Regulatory Peptides*, 41:149-56 (1992); Raufman, et al., *J. Biol. Chem.*, 267:21432-37 (1992); Singh, et al., *Regul. Pept.*, 53:47-59 (1994)). The use of the insulinotropic activities of exendin-3 and exendin-4 for the treatment of diabetes mellitus and the prevention of hyperglycemia have been proposed (Eng, U.S. Pat. No. 5,424,286).

Truncated exendin peptides such as exendin[9-39], a carboxyamidated molecule, and fragments 3-39 through 9-39 have been reported to be potent and selective antagonists of GLP-1 (Goke, et al., J. Biol. Chem., 268:19650-55 (1993); Raufman, J. P., et al., *J. Biol. Chem.*, 266:2897-902 (1991); Schepp, W., et al., *Eur. J. Pharm.*, 269:183-91 (1994); Montrose-Rafizadeh, et al., *Diabetes*, 45 (Suppl. 2):152A (1996)). Exendin[9-39] blocks endogenous GLP-1 in vivo, resulting in reduced insulin secretion (Wang, et al., *J. Clin. Invest.*, 95:417-21 (1995); D'Alessio, et al., *J. Clin. Invest.*, 97:133-38 (1996)). The receptor apparently responsible for the insulinotropic effect of GLP-1 has been cloned from rat pancreatic islet cells (Thorens, B., *Proc. Natl. Acad. Sci. USA* 89:8641-8645 (1992)). Exendins and exendin[9-39] bind to the cloned GLP-1 receptor (rat pancreatic-cell GLP-1 receptor: Fehmann H C, et al., *Peptides*, 15 (3): 453-6 (1994); human GLP-1 receptor: Thorens B, et al., *Diabetes*, 42 (11): 1678-82

(1993)). In cells transfected with the cloned GLP-1 receptor, exendin-4 is an agonist, i.e., it increases cAMP, while exendin [9-39] is an antagonist, i.e., it blocks the stimulatory actions of exendin-4 and GLP-1. Id.

Certain exendin compounds useful in the present methods include those disclosed in PCT/US98/16387, PCT/US98/24210, and PCT/US98/24273, all of which are herein incorporated by reference in their entireties.

In one embodiment an exendin analog can have one or more amino acid substitutions, deletions, inversion, or additions compared to a native or naturally occurring exendin. Thus, exendin analogs can have an amino acid sequence that has one or more amino acid substitutions, additions or deletions as compared with a naturally occurring exendin, for example, exendin-4. In one embodiment, an exendin analog has an amino acid sequence that has about 30 or less, 25 or less, 20 or less, 15 or less, 10 or less, 5 or less, 4 or less, 3 or less, 2 or less, or 1 or less substitutions, additions or deletions as compared to a naturally occurring exendin, such as exendin-4.

Certain exendin compounds useful in the present methods include those disclosed in PCT/US98/16387, PCT/US98/24210, and PCT/US98/24273, all of which are herein incorporated by reference in their entireties. More particularly, exendin compounds include exendin peptide analogs in which one or more naturally occurring amino acids are eliminated or replaced with another amino acid(s). Preferred exendin compounds are agonist analogs of exendin4. In addition to exendin-3 [His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser] [SEQ ID NO: 1], and exendin-4 [His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser] [SEQ ID NO: 2], particular exendin compounds include exendin-4 (1-30) [His Gly Glu Gly Thr Phe Thr Ser Asp Leu Ser Lys Gln Met Glu Glu Glu Ala Val Arg Leu Phe Ile Glu Trap Leu Lys Asn Gly Gly] [SEQ ID NO: 3], exendin-4 (1-30) amide [His Gly Glu Gly Thr Phe Thr Ser Asp Leu Ser Lys Gln Met Glu Glu Glu Ala Val Arg Leu Phe Ile Glu Trp Leu Lys Asn Gly Gly-$NH_2$] [SEQ ID NO: 4], exendin-4 (1-28) amide [His Gly Glu Gly Thr Phe Thr Ser Asp Leu Ser Lys Gln Met Glu Glu Glu Ala Val Arg Leu Phe Ile Glu Trp Leu Lys Asn-$NH_2$] [SEQ ID NO: 5], $^{14}$Leu, $^{25}$Phe exendin-4 [His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-$NH_2$] [SEQ ID NO: 6], $^{14}$Leu, $^{25}$Phe exendin-4 (1-28) amide [His Gly Glu Gly Thr Phe Thr Ser Asp Leu Ser Lys Gln Leu Glu Glu Glu Ala Val Arg Leu Phe Ile Glu Phe Leu Lys Asn-$NH_2$] [SEQ ID NO: 7], and $^{14}$Leu, $^{22}$Ala, $^{25}$Phe exendin-4 (1-28) amide [His Gly Glu Gly Thr Phe Thr Ser Asp Leu Ser Lys Gln Leu Glu Glu Glu Ala Val Arg Leu Ala Ile Glu Phe Leu Lys Asn-$NH_2$] [SEQ ID NO: 9], and those described in International Application No. PCT/US98/16387, filed Aug. 6, 1998, entitled, "Novel Exendin Agonist Compounds," including compounds of the formula (I):

(SEQ ID NO: 62)
Xaa$_1$ Xaa$_2$ Xaa$_3$ Gly Thr Xaa$_6$ Xaa$_7$ Xaa$_8$ Xaa$_9$ Xaa$_{10}$

Ser Lys Gln Xaa$_{14}$ Glu Glu Glu Ala Val Arg Leu

Xaa$_{22}$ Xaa$_{23}$ Xaa$_{24}$ Xaa$_{25}$ Leu Lys Asn Gly Gly Xaa$_{31}$

Ser Ser Gly Ala Xaa$_{36}$ Xaa$_{37}$ Xaa$_{38}$ Xaa$_{39}$, wherein Xaa$_1$ is His, Arg or Tyr; Xaa$_2$ is Ser, Gly, Ala or Thr; Xaa$_3$ is Asp or Glu; Xaa$_6$ is Phe, Tyr or naphthylalanine; Xaa$_7$ is Thr or Ser; Xaa$_8$ is Ser or Thr; Xaa$_9$ is Asp or Glu; Xaa$_{10}$ is Leu, Ile, Val, pentylglycine or Met; Xaa$_{14}$ is Leu, Ile, pentylglycine, Val or Met; Xaa$_{22}$ is Phe, Tyr or naphthylalanine; Xaa$_{23}$ is Ile, Val, Leu, pentylglycine, tert-butylglycine or Met; Xaa$_{24}$ is Glu or Asp; Xaa$_{25}$ is Trp, Phe, Tyr, or naphthylalanine; Xaa$_{31}$, Xaa$_{36}$, Xaa$_{37}$ and Xaa$_{38}$ are independently Pro, homoproline, 3Hyp, 4Hyp, thioproline, N-alkylglycine, N-alkylpentylglycine or N-alkylalanine; Xaa$_{39}$ is Ser, Thr or Tyr; wherein the C-terminus of the peptide is modified by —Z, wherein Z is —OH or —$NH_2$; with the proviso that the compound is not exendin-3 or exendin-4.

With reference to formula (I), preferred N-alkyl groups for N-alkylglycine, N-alkylpentylglycine and N-alkylalanine include lower alkyl groups, for example, of 1 to about 6 carbon atoms, or of 1 to 4 carbon atoms. Suitable compounds include those listed in FIGS. 9A and 9B.

Particular exendin compounds of formula (I) include those wherein Xaa$_1$ is His or Tyr, or more particularly, Xaa$_1$ is His.

Particular are those compounds of formula (I) wherein Xaa$_2$ is Gly.

Particular are those compounds of formula (I) wherein Xaa$_{14}$ is Leu, pentylglycine, or Met.

Particular compounds of formula (I) include those wherein Xaa$_{25}$ is Trp or Phe.

Also included are compounds of formula (I) where Xaa$_6$ is Phe or naphthylalanine; Xaa$_{23}$ is Ile or Val and Xaa$_{31}$, Xaa$_{36}$, Xaa$_{37}$ and Xaa$_{38}$ are independently selected from Pro, homoproline, thioproline or N-alkylalanine. In one embodiment, N-alkylalanine has a N-alkyl group of 1 to about 6 carbon atoms.

According to another aspect, compounds of formula (I) include those where Xaa$_{36}$, Xaa$_{37}$ and Xaa$_{38}$ are the same amino acid reside.

Included are compounds of formula (I) wherein Xaa$_{39}$ is Ser or Tyr, more preferably Ser.

According to one aspect, included are compounds of formula (I) wherein Xaa$_1$ is His or Tyr, more particularly His; Xaa$_2$ is Gly; Xaa$_6$ is Phe or naphthylalanine; Xaa$_{14}$ is Leu, pentylglycine or Met; Xaa$_{22}$ is Phe or naphthylalanine; Xaa$_{23}$ is Ile or Val; Xaa$_{31}$, Xaa$_{36}$, Xaa$_{37}$ and Xaa$_{38}$ are independently selected from Pro, homoproline, thioproline or N-alkylalanine; and Xaa$_{39}$ is Ser or Tyr, more particularly Ser. In one embodiment, Z is —$NH_2$.

According to one aspect, compounds include those of formula (I) wherein: Xaa$_1$ is His or Arg; Xaa$_2$ is Gly; Xaa$_3$ is Asp or Glu; Xaa$_6$ is Phe or napthylalanine; Xaa$_7$ is Thr or Ser; Xaa$_8$ is Ser or Thr; Xaa$_9$ is Asp or Glu; Xaa$_{10}$ is Leu or pentylglycine; Xaa$_{14}$ is Leu or pentylglycine; Xaa$_{22}$ is Phe or naphthylalanine; Xaa$_{23}$ is Ile, Val or t-butyltylglycine; Xaa$_{24}$ is Glu or Asp; Xaa$_{25}$ is Trp or Phe; Xaa$_{31}$, Xaa$_{36}$, Xaa$_{37}$, and Xaa$_{38}$ are independently Pro, homoproline, thioproline, or N-methylalanine; Xaa$_{39}$ is Ser or Tyr: and Z is —OH or —$NH_2$; with the proviso that the compound does not have the formula of either SEQ. ID. NOS. 1 or 2. In one embodiment, Z is —$NH_2$. Exemplary compounds include those having the amino acid sequence of SEQ. ID. NOS. 9, 10, 21, 22, 23, 26, 28, 34, 35 and 39.

According to one aspect, provided are compounds of formula (I) where Xaa$_{14}$ is Leu, Ile, Val or pentylglycine, more particularly Leu or pentylglycine, and Xaa$_{13}$ is Phe, Tyr or naphthylalanine, more particularly Phe or naphthylalanine.

With reference to formula (I), one embodiment of Z is —$NH_2$.

Exendin compounds also include compounds of the formula (II):

```
Xaa1 Xaa2 Xaa3 Gly Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

Xaa27 Xaa28,
``` wherein: $Xaa_1$ is His, Arg or Tyr; $Xaa_2$ is Ser, Gly, Ala or Thr; $Xaa_3$ is Ala, Asp or Glu; $Xaa_5$ is Ala or Thr; $Xaa_6$ is Ala, Phe, Tyr or naphthylalanine; $Xaa_7$ is Thr or Ser; $Xaa_8$ is Ala, Ser or Thr; $Xaa_9$ is Asp or Glu; $Xaa_{10}$ is Ala, Leu, Ile, Val, pentylglycine or Met; $Xaa_{11}$ is Ala or Ser; $Xaa_{12}$ is Ala or Lys; $Xaa_{13}$ is Ala or Gln; $Xaa_{14}$ is Ala, Leu, Ile, pentylglycine, Val or Met; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Ala, Phe, Tyr or naphthylalanine; $Xaa_{23}$ is Ile, Val, Leu, pentylglycine, tert-butylglycine or Met; $Xaa_{24}$ is Ala, Glu or Asp; $Xaa_{25}$ is Ala, Trp, Phe, Tyr or naphthylalanine; $Xaa_{26}$ is Ala or Leu; $Xaa_{27}$ is Ala or Lys; $Xaa_{28}$ is Ala or Asn; wherein the C-terminus of the peptide is modified by —$Z_1$, wherein $Z_1$ is —OH or —$NH_2$, or wherein the C-terminus of the peptide further includes Gly, Gly Gly (SEQ ID NO:63), Gly Gly $Xaa_{31}$ (SEQ ID NO:64), Gly Gly $Xaa_{31}$ Ser (SEQ ID NO:65), Gly Gly $Xaa_{31}$ Ser Ser (SEQ ID NO:66), Gly Gly $Xaa_{31}$ Ser Ser Gly (SEQ ID NO:67), Gly Gly $Xaa_{31}$ Ser Ser Gly Ala (SEQ ID NO:68), Gly Gly $Xaa_{31}$ Ser Ser Gly Ala $Xaa_{36}$ (SEQ ID NO:69), Gly Gly $Xaa_{31}$ Ser Ser Gly Ala $Xaa_{36}$ $Xaa_{37}$ (SEQ ID NO:70) or Gly Gly $Xaa_{31}$ Ser Ser Gly Ala $Xaa_{36}$ $Xaa_{37}$ $Xaa_{38}$ (SEQ ID NO:71); $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine, and the C-terminus of the peptide is modified by —$Z_2$, wherein $Z_2$ is —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa14$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala.

With reference to formula (II), exemplary N-alkyl groups for N-alkylglycine, N-alkylpentylglycine and N-alkylalanine include lower alkyl groups of 1 to about 6 carbon atoms, or of 1 to 4 carbon atoms.

Exendin compounds of formula (II) include those wherein $Xaa_1$ is His or Tyr. More particularly, $Xaa_1$ is His.

Included are those compounds of formula (II) wherein $Xaa_2$ is Gly.

Included are those compounds of formula (II) wherein $Xaa_{14}$ is Leu, pentylglycine or Met.

Included compounds of formula (II) are those wherein $Xaa_{25}$ is Trp or Phe.

Included compounds of formula (II) are those where $Xaa_6$ is Phe or naphthylalanine; $Xaa_{22}$ is Phe or naphthylalanine and $Xaa_{23}$ is Ile or Val.

Included are compounds of formula (II) wherein $Xaa_{31}$, $Xaa_{36}$, $Xaa_{37}$ and $Xaa_{38}$ are independently selected from Pro, homoproline, thioproline and N-alkylalanine.

With reference to formula (II), $Z_1$ may be —$NH_2$.

With reference to formula (II), $Z_2$ may be —$NH_2$.

According to one aspect, included are compounds of formula (II) wherein $Xaa_1$ is His or Tyr, more particularly His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. $Z_1$ may be —$NH_2$.

According to another aspect, compounds include those of formula (II) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or naphthylalanine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Compounds include those having the amino acid sequence of SEQ. ID. NOS. 40-61.

According to one aspect, provided are compounds of formula (II) where $Xaa_{14}$ is Leu, Ile, Val or pentylglycine, more particularly Leu or pentylglycine, and $Xaa_{25}$ is Phe, Tyr or naphthylalanine, more particularly Phe or naphthylalanine.

Exendin compounds also include compounds of the formula (III):

```
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

Xaa27 Xaa28,
``` wherein $Xaa_1$ is His, Arg, Tyr, Ala, Norval, Val, or Norleu; $Xaa_2$ is Ser, Gly, Ala or Thr; $Xaa_3$ is Ala, Asp or Glu; $Xaa_4$ is Ala, Norval, Val, Norleu or Gly; $Xaa_5$ is Ala or Thr; $Xaa_6$ is Ala, Phe, Tyr or naphthylalanine; $Xaa_7$ is Thr or Ser; $Xaa_8$ is Ala, Ser or Thr; $Xaa_9$ is Ala, Norval, Val, Norleu, Asp or Glu; $Xaa_{10}$ is Ala, Leu, Ile, Val, pentylglycine or Met; $Xaa^{11}$ is Ala or Ser; $Xaa_{12}$ is Ala or Lys; $Xaa_{13}$ is Ala or Gln; $Xaa_{14}$ is Ala, Leu, Ile, pentylglycine, Val or Met; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe, Tyr or naphthylalanine; $Xaa_{23}$ is Ile, Val, Leu, pentylglycine, tert-butylglycine or Met; $Xaa_{24}$ is Ala, Glu or Asp; $Xaa_{25}$ is Ala, Trp, Phe, Tyr or naphthylalanine; $Xaa_{26}$ is Ala or Leu; $Xaa_{27}$ is Ala or Lys; $Xaa_{28}$ is Ala or Asn; wherein the C-terminus of the peptide is modified by —$Z_1$, wherein $Z_1$ is —OH or —$NH_2$, or wherein the C-terminus of the peptide further includes Gly, Gly Gly, Gly Gly $Xaa_{31}$, Gly Gly $Xaa_{31}$ Ser (SEQ ID NO:72), Gly Gly $Xaa_{31}$ Ser Ser (SEQ ID NO:73), Gly Gly $Xaa_{31}$ Ser Ser Gly (SEQ ID NO:74) Gly Gly $Xaa_{31}$ Ser Ser Gly Ala (SEQ ID NO:75), Gly Gly $Xaa_{31}$ Ser Ser Gly Ala $Xaa_{36}$ (SEQ ID NO:76), Gly Gly $Xaa_{31}$ Ser Ser Gly Ala $Xaa_{36}$ $Xaa_{37}$ (SEQ ID NO:77), Gly Gly $Xaa_{31}$ Ser Ser Gly Ala $Xaa_{36}$ $Xaa_{37}$ $Xaa_{38}$ (SEQ ID NO:78) or Gly Gly $Xaa_{31}$ Ser Ser Gly Ala $Xaa_{36}$ $Xaa_{37}$ $Xaa_{38}$ $Xaa_{39}$ (SEQ ID NO:79); wherein $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; $Xaa_{39}$ is Ser, Thr, Lys or Ala, and the C-terminus of the peptide is modified by —$Z_2$, wherein $Z_2$ is —OH or —$NH_2$; provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala.

In another aspect, Z is one or more additional amino acids that do not change the function of the exendin as described herein with an —OH or $NH_2$ at the carboxy terminus. Exemplary additional amino acids are between 2 and 10 additional amino acids, between 3 and 7 additional amino acids, and about 5 additional amino acids.

In another embodiment, CICs include GLP-1 peptides. By way of non-limiting examples, a GLP-1 peptide includes GLP-1 (1-37), GLP-1 (1-36) amide, GLP-1 (7-37), GLP-1 (7-36) amide (known in the art as "GLP-1"), and GLP-1(9-36). Other exemplary GLP-1 peptides include GLP-1 agonists described in WO 03/084563, incorporated herein by reference in its entirety. In one embodiment, a GLP-1 peptide used in the methods provided herein is a long-acting GLP-1 analog. A long acting analog refers to any GLP-1 peptide that has a longer in vivo half-life than GLP-1. Such long-acting GLP-1 analogs are known in the art and described herein.

A CIC also includes any biologically active analogs, including variants and derivatives, of GLP-1 peptides. A biologically active GLP-1 analog, including a variant or derivative thereof, can possess GLP-1 biological activity that is more potent, less potent or equally potent as compared to the biological activity of a native GLP-1. Biologically active GLP-1 analogs also include those molecules that can exhibit GLP-1 activity upon cleavage, translation, or any other processing that occurs upon administration of the GLP-1 analog.

In an embodiment, a GLP-1 analog includes any peptides that are formed by conservative amino acid substitution of a GLP-1 peptide. For example, it is well known in the art that one or more amino acids in a sequence, such as an amino acid sequence for GLP-1, can be substituted with other amino acid(s), the charge and polarity of which are similar to that of the native amino acid. Hydropathic index of amino acids can be considered when making amino acid changes. The importance of the hydropathic amino acid index in conferring interactive biological function on a protein is generally understood in the art (Kyte and Doolittle, *J. Mol. Biol.* 157:105-132 (1982)). It is also understood in the art that the conservative substitution of amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. In making such changes, the substitution of amino acids whose hydrophilicity values are within ±2 is preferred, those that are within ±1 are particularly preferred, and those within ±0.5 are even more particularly preferred.

Due to the degeneracy of the genetic code, different nucleotide codons can encode a particular amino acid. Accordingly, the methods provided herein contemplates that a nucleic acid molecule encoding a GLP-1 analog can have any codon usage that encodes a GLP-1 analog. A host cell often exhibits a preferred pattern of codon usage. In a preferred embodiment, the codon usage of a nucleotide sequence encoding a GLP-1 reflects a preferred codon usage for a host in which the GLP-1 analog will be used.

In another embodiment, a GLP-1 analog has an amino acid sequence that has one or more amino acid substitutions, additions or deletions as compared with a GLP-1 peptide, preferably GLP-1. In one embodiment, a GLP-1 analog has an amino acid sequence that has about 30 or less, 25 or less, 20 or less, 15 or less, 10 or less, 5 or less, 4 or less, 3 or less, 2 or less, or 1 or less substitutions, additions, or deletions as compared to a GLP-1 peptide. Various GLP-1 analogs are generally known in the art and are available to the skilled artisan.

In another embodiment, a GLP-1 analog has at least 60%, at least 70%, at least 80%, at least 90% or at least 95% sequence identity with a naturally occurring GLP-1. Identity, as is well understood in the art, is a relationship between two or more polypeptide sequences or two or more polynucleotide sequences, as determined by comparing the sequences. In the art, identity also means the degree of sequence relatedness between polypeptide or polynucleotide sequences, as determined by the match between strings of such sequences. Identity can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76-80 (1994); Birren, et al., *Genome Analysis*, 1: 543-559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403-410 (1990)). The well-known Smith Waterman algorithm can also be used to determine identity.

A CIC includes GLP-1 agonists and exendin agonists. The term "agonist" includes analogs. More particularly, as used herein, an "analog" is defined as a molecule having one or more amino acid substitutions, deletions, inversions, or additions compared with a native peptide such as a GLP-1 or exendin. The term "agonist" also includes derivatives. A "derivative" is defined as a molecule having the amino acid sequence of a native peptide or of an analog of the native peptide, but additionally having a chemical modification of one or more of its amino acid side groups, alpha-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal carboxy group include, without limitation, the amide, lower alkyl amide, dialkyl amide, and lower alkyl ester modifications. An exemplary lower alkyl is a C1-C4 alkyl. Furthermore, one or more side groups, or terminal groups, may be protected by protective groups known to the ordinarily-skilled protein chemist. The α-carbon of an amino acid may be mono- or dimethylated.

GLP-1 analogs known in the art include, for example, GLP-1(7-34) and GLP-1(7-35), Gln$^9$-GLP-1(7-37), D-Gln$^9$-GLP-1(7-37), Thr$^{16}$-Lys$^{18}$-GLP-1(7-37), and Lys$^{18}$-GLP-1(7-37). Other preferred GLP-1 analogs include: Gly$^8$-GLP-1(7-36)NH$_2$, Gln$^9$-GLP-1 (7-37), D-Gln$^9$-GLP-1 (7-37), acetyl-Lys$^9$-GLP-1(7-37), Thr$^9$-GLP-1(7-37), D-Thr$^9$-GLP-1 (7-37), Asn$^9$-GLP-1 (7-37), D-Asn$^9$-GLP-1 (7-37), Ser$^{22}$-Arg$^{23}$-Arg$^{24}$-Gln$^{26}$-GLP-1(7-37), Thr$^{16}$-Lys$^{15}$-GLP-1 (7-37), Lys$^{13}$-GLP-1(7-37), Arg$^{23}$-GLP-1(7-37), Arg$^{24}$-GLP-1(7-37), and the like (see, e.g., WO 91/11457).

Other GLP-1 analogs are disclosed in U.S. Pat. No. 5,545,618 which is incorporated herein by reference. A particular group of GLP-1 analogs and derivatives include those disclosed in U.S. Pat. No. 6,747,006, which is herein incorporated by reference in its entirety. The use of a molecule described in U.S. Pat. No. 5,188,666, which is expressly incorporated by reference, is also contemplated. Another group of molecules useful in the disclosed methods includes compounds described in U.S. Pat. No. 5,512,549, which is expressly incorporated herein by reference.

Another group of active compounds for use in the present methods is disclosed in WO 91/11457, and consists essentially of GLP-1(7-34), GLP-1(7-35), GLP-1(7-36), or GLP-1(7-37), or the amide form thereof, and pharmaceutically-acceptable salts thereof, having at least one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

Because the enzyme, dipeptidyl-peptidase IV (DPP IV), may be responsible for the observed rapid in vivo inactivation of administered GLP-1, (see, e.g., Mentlein, R., et al., *Eur. J. Biochem.*, 214:829-835 (1993)), administration of GLP-1 analogs and derivatives that are protected from the activity of DPP IV are included, for example, the administration of Gly$^8$-GLP-1(7-36)NH$_2$, Val$^8$-GLP-1(7-37)OH, α-methyl-Ala$^8$-GLP-1(7-36)NH$_2$, and Gly$^8$-Gln$^{21}$-GLP-1(7-37)OH, or pharmaceutically-acceptable salts thereof. Alternatively or additionally, a DPPIV inhibitor may also be administered.

A CIC can be obtained from any source. In one embodiment, a CIC can be obtained from an organism, such as a mouse, a rat, a lizard, or a human. It is also contemplated herein that a CIC can be obtained by any method or combination of methods known to the skilled artisan. In an illustrative embodiment, a CIC can be isolated by collection of a secretion, by extraction, by purification, or by any combination such of methods. In another embodiment, a CIC can be identified and purified by the use of monoclonal, polyclonal, or any combination of antibodies. Antibodies such as ABGA1178 detect intact, unspliced GLP-1 (1-37) or N-terminally truncated GLP-1 (7-37) or GLP-1. In addition, other antibodies detect at the very end of the C-terminus of the precursor molecule (See e.g., Osrkov et al., *J. Clin. Invest* 87: 415-423 (1991)).

In another embodiment, a CIC can be obtained by any recombinant means. A recombinant CIC includes any molecule that is, or results, however indirectly, from human manipulation of a nucleic or amino acid molecule. In one embodiment, a recombinant molecule is a recombinant human peptide.

In yet another embodiment, a CIC may be a small molecule which is an incretin mimetic or can bind or activate a GLP-1 receptor, and has the ability to affect cardiac function or cardiac physiology or anatomy as herein described or known in the art, and may be synthesized in any manner known in the art.

In another embodiment, the use of DPP IV inhibitors to decrease or eliminate the inactivation of endogenous or exogenous GLP-1, GLP-1 analog, or GLP-1 agonist is also contemplated. DPP IV inhibitors can be administered alone or in combination with a CIC. As such, it is contemplated that active CICs may be increased by the inhibition of DPP IV. Inhibitors of DPP IV are known to the skilled artisan and include, by way of non-limiting example, 2-cyanopyrrolidines. See e.g., Fukushima, H., et al., *Bioorg. Med. Chem. Lett.* 14(22): 6053-6061 (2004). Non-limiting exemplary DPP IV inhibitors include valine-pyrrolidide (Marguet, D., et al., *Proc. Natl. Acad. Sci. USA* 97(12): 6874-6879 (2000)), isoleucine thiazolidide (Pederson, R. A., et al., *Diabetes* 47: 1253-1258 (1998), and NVP-DPP728 (Balkan, B., et al., *Diabetologia* 42(11): 1324-1331 (1999)). DPP IV inhibitors including ketopyrrolidines and ketoazetidines have been discussed in the literature (Ferraris, D., et al., *Bioorg. Med. Chem. Lett.* 14(22): 5579-5583 (2004)). Metformin and pioglitazone have been proposed to reduce DPP IV activity in vivo. (Kenhard, J. M., et al., *Biochem. Biophys. Res. Commun.* 324(1):92-97 (2004). Literature reports further describe optimization of a proline derived homophenylalanine 3 to produce a potent DPP IV inhibitor. See Edmondson, S. D., et al., Bioorg. Med. Chem. Lett. 14(20): 5151-5155 (2004).

CICs may be formulated as pharmaceutical compositions for use in conjunction with the methods disclosed herein. The pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, or from about pH 3 to about pH 7, depending on the formulation and route of administration. In alternative embodiments, the pH may be adjusted to a range from about pH 5.0 to about pH 8.0, from about pH 3.0 to about pH 6.0, or from about pH 4.0 to about pH 5.0.

In an embodiment, a pharmaceutical composition provided herein comprises an effective amount of at least one CIC, together with one or more pharmaceutically acceptable excipients. Optionally, a pharmaceutical composition may include a second active ingredient useful in the prevention or treatment of cardiac remodeling.

The pharmaceutical compositions may be formulated for administration in any manner known in the art. By way of example, when formulated for oral administration or parenteral administration, the pharmaceutical composition is most typically a solid, liquid solution, emulsion or suspension, while inhalable formulations for pulmonary or nasal administration are generally liquids or powders. A pharmaceutical composition may also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as a CIC. The term refers to any pharmaceutical excipient that may be administered without undue toxicity. Pharmaceutically acceptable excipients are determined in part by the particular composition being administered, as well as by the particular method used to administer the composition. Accordingly, there exist a wide variety of suitable formulations of pharmaceutical compositions for use in the methods provided herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

More particularly, when intended for oral use, e.g., tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, the pharmaceutical composition of the methods provided herein may be formulated as a suspension comprising a CIC in admixture with at least one pharmaceutically acceptable excipient suitable for the manufacture of a suspension. In yet another embodiment, a CIC may be formulated as dispersible powder and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical composition of the methods provided herein may also be in the form of an oil-in-water emulsion. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

In another embodiment, the pharmaceutical composition of the methods provided herein may be formulated as a sterile injectable preparation, such as a sterile injectable aqueous emulsion or oleaginous suspension. This emulsion or suspension may be formulated according to the known art using those suitable dispersing or wetting agents and suspending agents such as those that have been mentioned above. In another embodiment, the sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Certain CICs may be substantially insoluble in water and sparingly soluble in most pharmaceutically acceptable protic solvents and in vegetable oils. However, the compounds may be soluble in medium chain fatty acids (e.g., caprylic and capric acids) or triglycerides and have high solubility in propylene glycol esters of medium chain fatty acids. Also contemplated for use in the methods disclosed herein are compositions, which have been modified by substitutions or additions of chemical or biochemical moieties which make them more suitable for delivery (e.g., increase solubility, bioactivity, palatability, decrease adverse reactions, etc.), for example by esterification, glycation, PEGylation, etc.

A CIC may also be formulated for oral administration in a self-emulsifying drug delivery system (SEDDS). Lipid-based formulations such as SEDDS are particularly suitable for low solubility compounds, and can generally enhance the oral bioavailability of such compounds.

In an alternative embodiment, cyclodextrins may be added as aqueous solubility enhancers. Cyclodextrins include hydroxypropyl, hydroxyethyl, glucosyl, maltosyl and maltotriosyl derivatives of □-, □-, and □-cyclodextrin. An exemplary cyclodextrin solubility enhancer is hydroxypropyl-□-cyclodextrin (HPBC), which may be added to any of the above-described compositions to further improve the aqueous solubility characteristics of a GLP-1 molecule or agonist thereof. In one embodiment, the composition comprises 0.1% to 20% hydroxypropyl-□-cyclodextrin, for example 1% to 15% hydroxypropyl-□-cyclodextrin, or from 2.5% to 10% hydroxypropyl-□-cyclodextrin. The amount of solubility enhancer employed will depend on the amount of CIC in the composition.

Dosage and administration are adjusted to provide sufficient levels of the active agent(s) in a pharmaceutical composition or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Whether an administration is acute or chronic may also be considered in determining dosage. Long-acting pharmaceutical compositions may be administered every 3 to 4 days, every week, or once every two weeks depending on half-life and clearance rate of the particular formulation. In one embodiment, CICs used in the present methods are formulated for sustained release.

Exemplary treatment regimens include, but are not limited to, administration via injection to achieve a dose of from about 0.1 µg/kg to about 0.5 µg/kg or from about 0.005 µg/kg to about 0.2 µg/kg of the CIC. Other exemplary treatment regimens include, but are not limited to, administration via injection to achieve a dose of from about 1 µg/day to about 1 mg/day or from about 500 µg/day to about 12,000 µg/day of the CIC in a single or divided dose.

Still other exemplary treatment regimens include, but are not limited to, pulmonary administration to achieve a dose from about 100 µg/day to about 12,000 µg/day of the CIC in a single or divided dose; nasal administration to achieve a dose from about 10 µg/day to about 12,000 µg/day of the CIC in a single or divided dose; and buccal administration to achieve a dose from about 100 µg/day to about 12,000 µg/day of the CIC in a single or divided dose.

In another aspect, it is also possible to combine a CIC, with one or more other active ingredients useful in the prevention of cardiac remodeling. For example, a CIC may be combined with one or more other compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more CICs and one or more additional active ingredients by different routes. The skilled artisan will also recognize that a variety of active ingredients may be administered in combination with CIC that may act to augment or synergistically enhance the prevention, amelioration, attenuation, or delay of cardiac remodeling.

According to the methods provided herein, a CIC may be: (1) co-formulated and administered or delivered simultaneously in a combined formulation; (2) delivered by alternation or in parallel as separate formulations; or (3) by any other combination therapy regimen known in the art. When delivered in alternation therapy, the methods provided herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

EXAMPLES

Example 1

Treatment with a GLP-1 Molecule Reduces Cardiac Remodeling

Male Sprague-Dawley® rats (250-300 g) are anesthetized by using 5% isoflurane and a left thoracotomy was performed. The left main anterior descending artery (LAD) was ligated to induce myocardial infarction. In addition, sham animals (n=10) were subjected to the same surgical procedure without ligation of the LAD.

After two weeks, rats were treated with 2.5 pmol/kg/min GLP-1 (n=11) (GLPL), 25 pmol/kg/min GLP-1 (n=12) (GLPH), 1.67 pmol/kg/min an exendin agonist, AC3174, (n=12) (AC3174L), 5 pmol/kg/min exendin agonist (n=7) (AC3174H), or vehicle (n=14) via subcutaneous infusion for 11 weeks. Echocardiography was performed at the $3^{rd}$, $5^{th}$, $9^{th}$, and $13^{th}$ week of myocardial infarction. Left ventricular (LV) end systolic dimension (ESD) and diastolic dimension (EDD), LV systolic volume and diastolic volume, left atrial volume were recorded. At the $13^{th}$ week of MI, the hearts were excised, the LV mass were weighed and LV mass/body weight ratio was determined.

Figure 2:
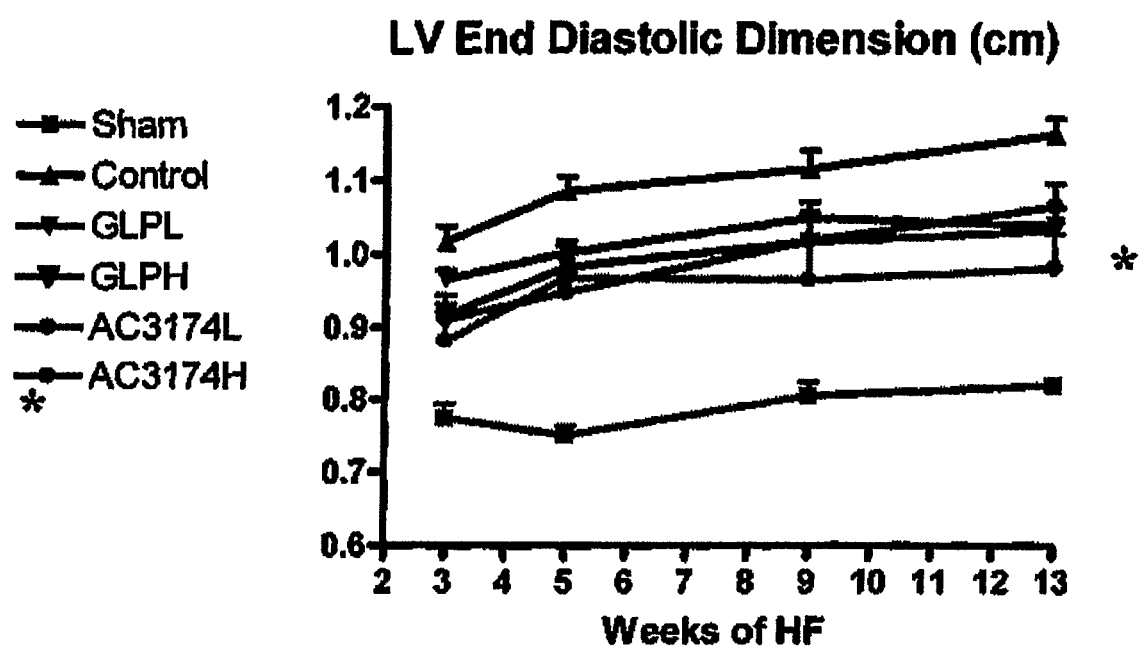
FIG. 2 demonstrates the effect of CICs on the enlargement of the heart chamber using LV end diastolic dimension analysis.
Figure 3:
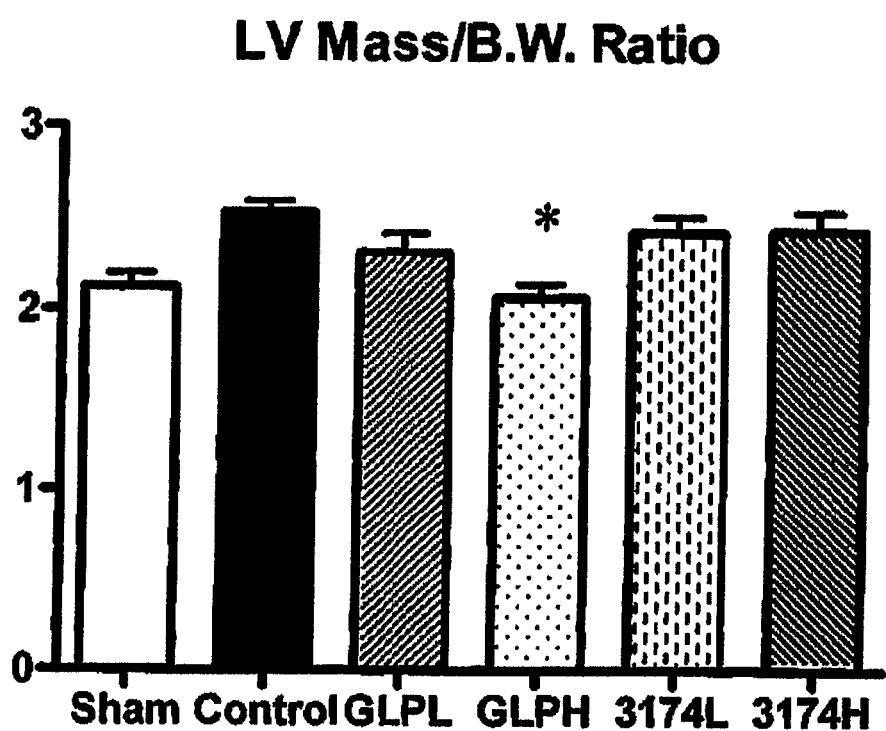
FIG. 3 demonstrates the effect of CICs on the LV Mass/body weight ratio.
Figure 4A:
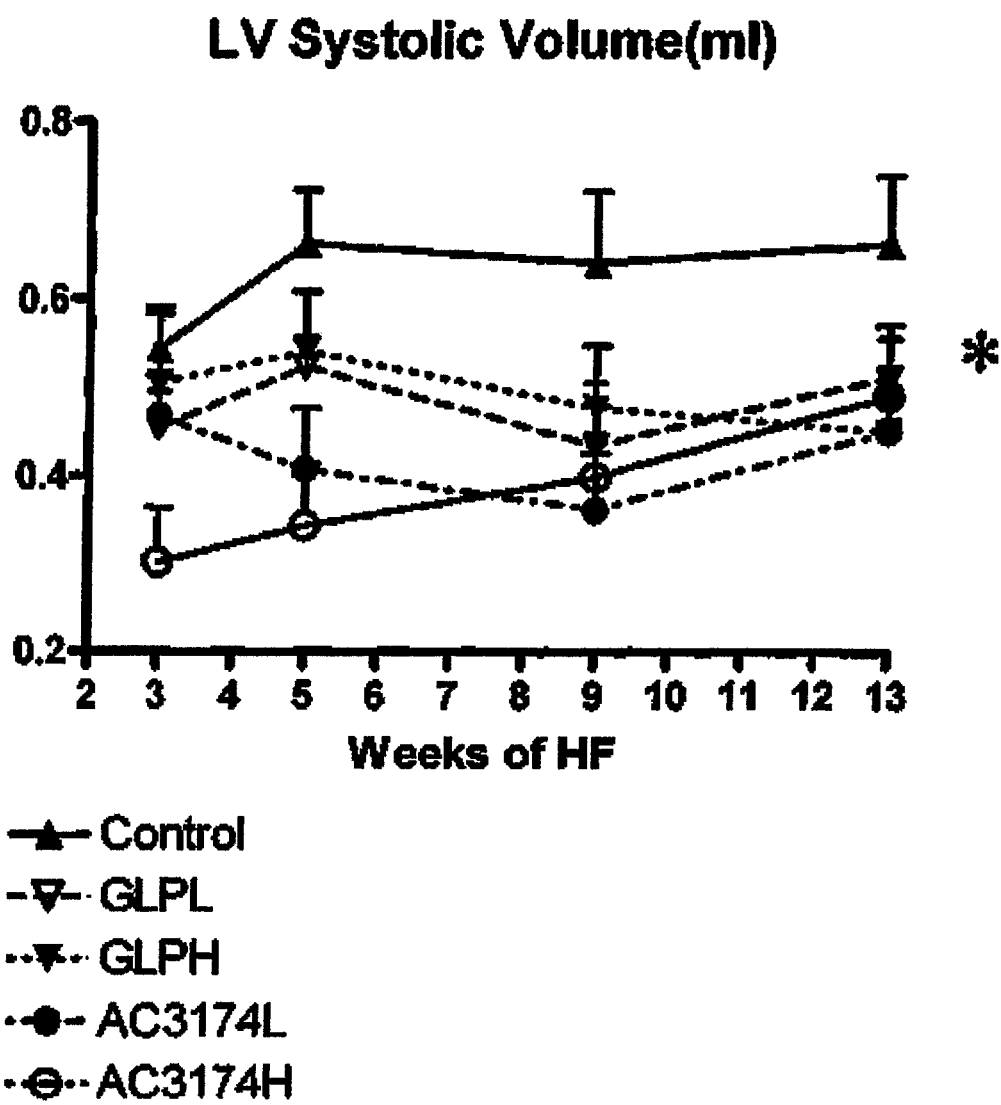
FIGS. 4A, 4B, and 4C demonstrate the effect of CICs on the enlargement of the LV and LA volume.
Figure 4B:
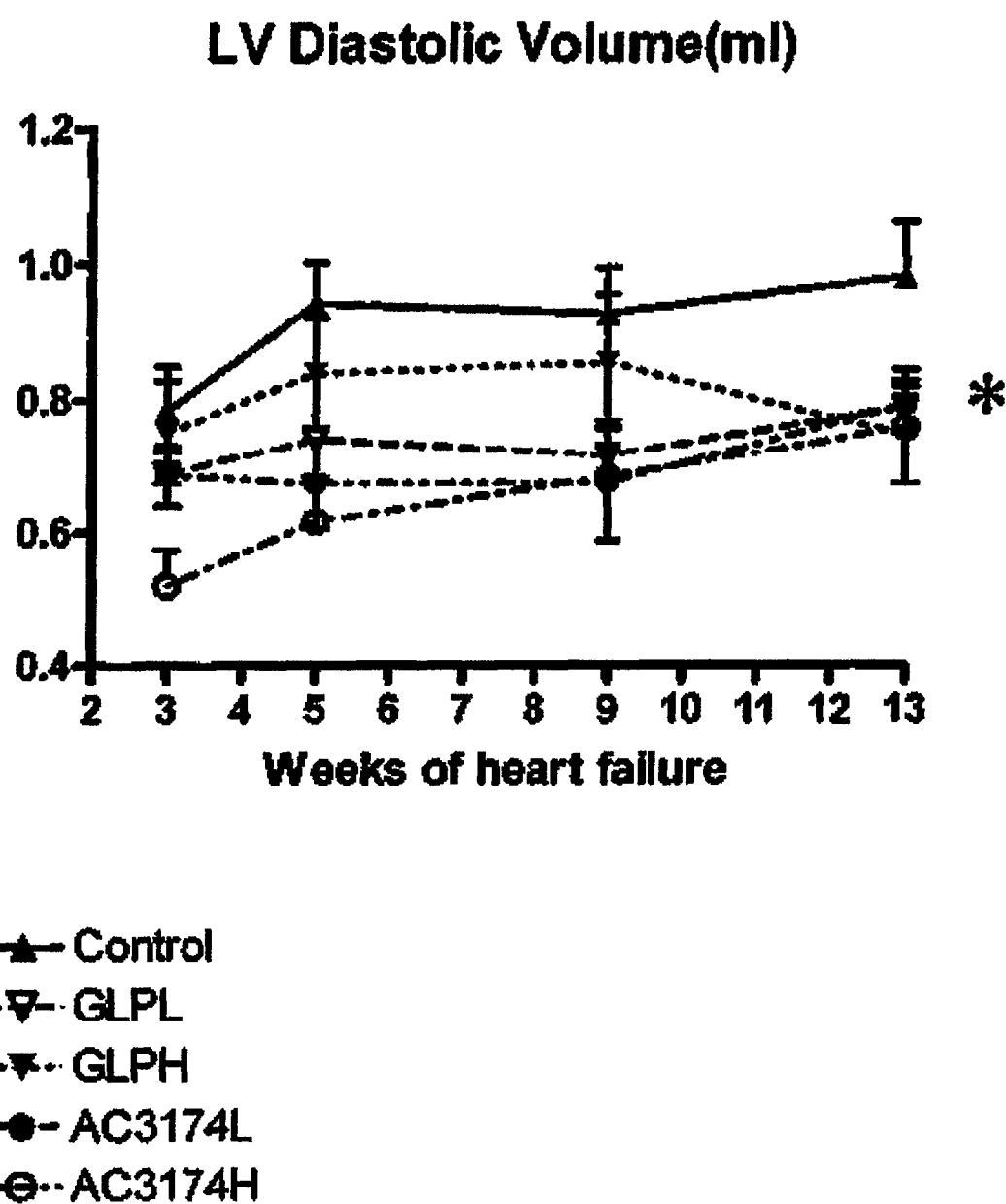
Figure 4C:
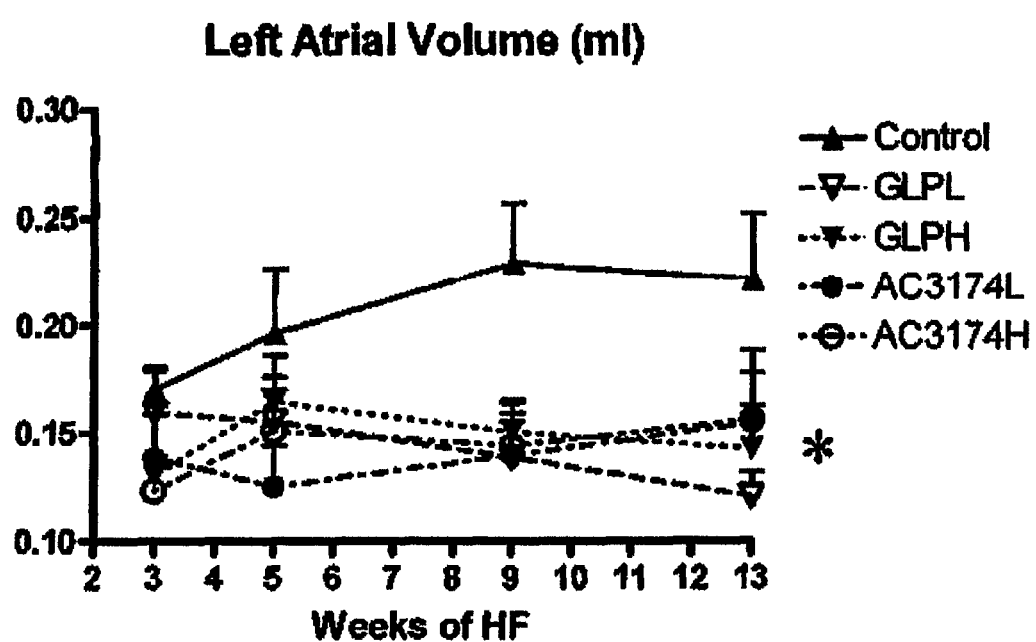
Figure 5:
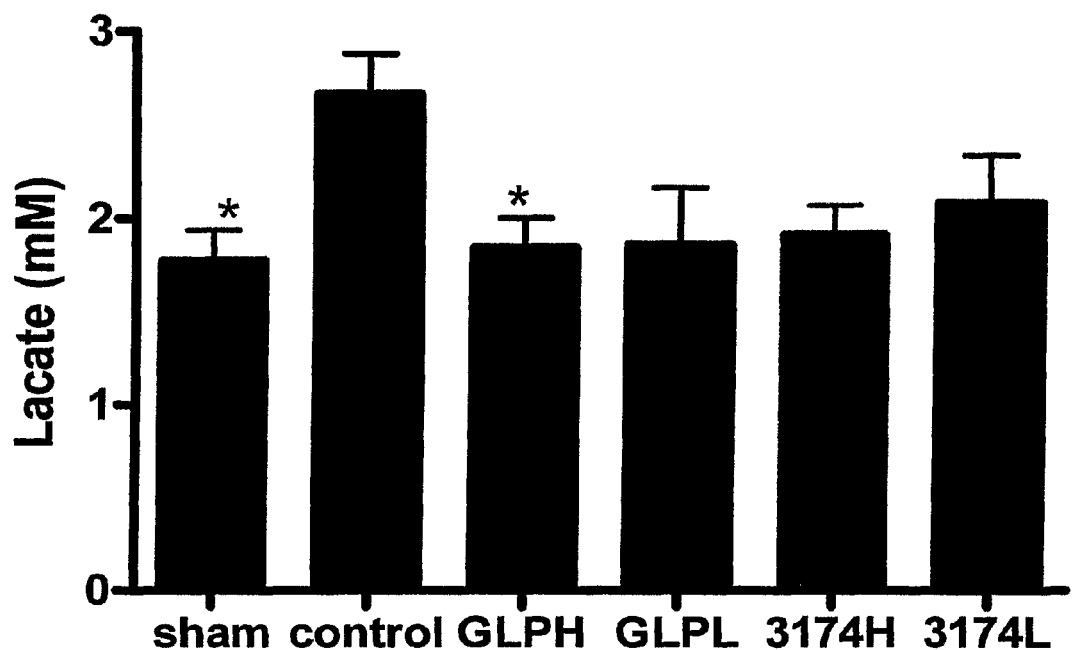
FIG. 5 demonstrates the effect of CICs on the baseline plasma lactate levels.
Figures 6A, 6B:
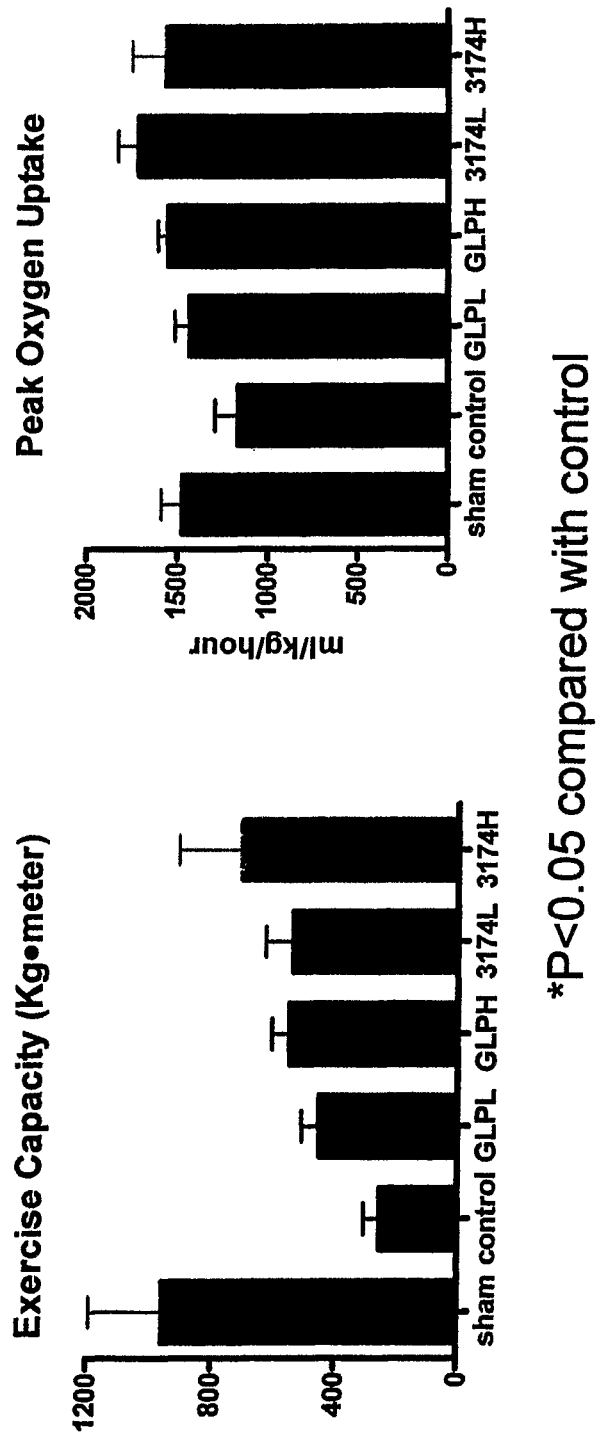
FIGS. 6A and 6B demonstrates the effect of CICs on exercise capacity and peak oxygen uptake.
Figure 7:
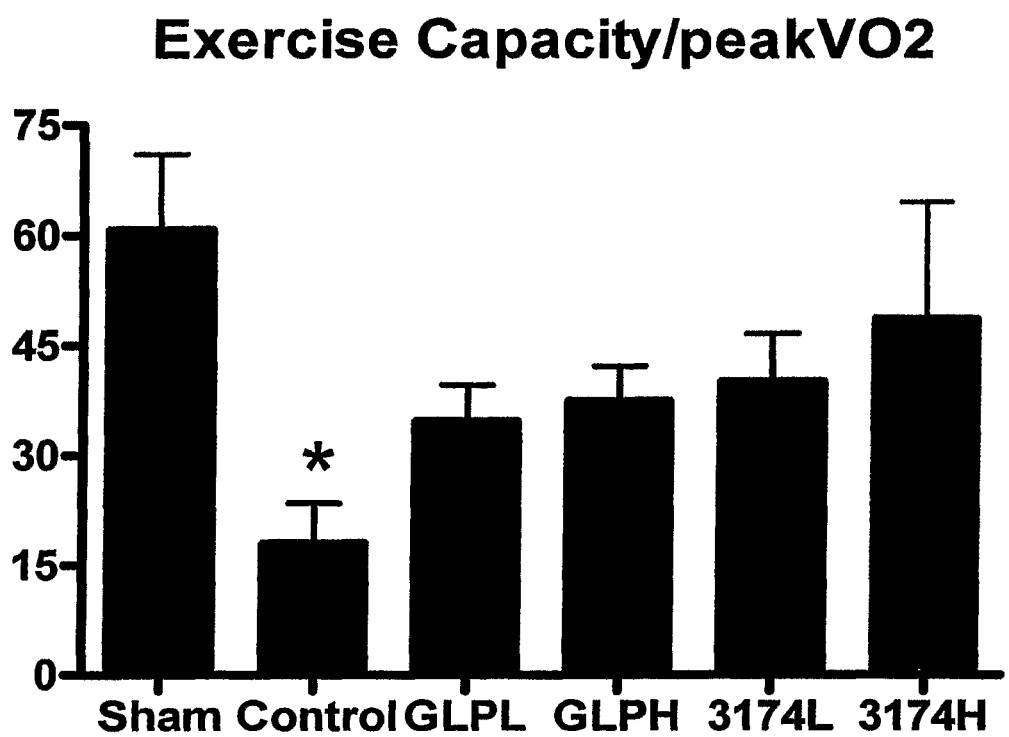
FIG. 7 demonstrates the effect of CICs on exercise capacity efficiency.
Figure 8A:
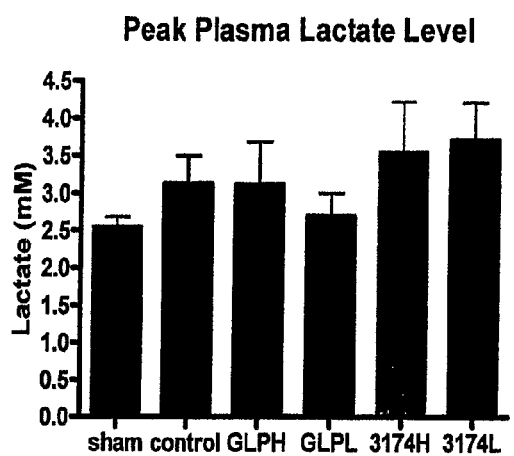
FIGS. 8A and 8B demonstrates the effect of CICs on the peak plasma lactate level and the exercise capacity/lactate ratio.
Figure 8B:
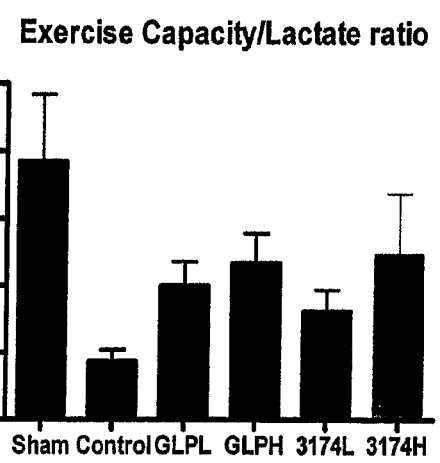

The results show that the E/A ratio is increased by 116% 9p<0.001) in the control group (vehicle only) at 13 weeks after MI, as compared to the sham group. Administration of GLP-1 or the exendin agonist at each dose prevented increases in these two indexes during CHF progression. The LVEDP increased by 97% (p<0.001) in the vehicle group as compared to the sham group. Administration of GLP-1 or the exendin agonist eliminated the LV end diastolic pressure (LVEDP) elevation. Cardiac output and +dp/dtmax in the control group was reduced by 19% (p<0.01) and 24% (p<0.05), respectively, as compared to the sham group. Administration of GLP-1 or the exendin agonist normalized both the cardiac output and contractility. LV mass, LV end diastolic dimension and systolic dimension increased during the progression of CHF. However, administration of GLP-1 or the exendin agonist significantly reduced such remodeling. Administration of 25 pmol/kg/min GLP-1 significantly reduced infarct size by 30% (p<0.05) compared to the control group. Further, administration of GLP-1 or the exendin agonist at each dose significantly improved exercise capacity (EC) and exercise efficiency (EC/VO2) during a treadmill test. The results of these tests are summarized in FIGS. 1-8 and Table 1. In sum, chronic treatment with GLP-1 or the exendin agonist AC3174 demonstrated cardioprotective effects in that MI-induced rat model that included slowed enlargement of LV chamber, improved cardiac diastolic and systolic function, improved exercise capacity and efficiency, attenuated baseline plasma lactate, improved exercise capacity/peak lactate ratio, reduced infarction size, attenuated LV weight, and improved insulin sensitivity.

TABLE 1

Whole body composition, heart, lung weight and infarct size in rats with or without CHF at 13

|  | Sham | Control | GLPL | GLPH | AC3174L | AC3174H |
|---|---|---|---|---|---|---|
| B.W, g | 511 ± 16 | 522 ± 17 | 523 ± 14 | 518 ± 12 | 493 ± 10 | 435 ± 15‡ |
| Fat mass, g | 58 ± 6 | 47 ± 6 | 45 ± 6 | 51 ± 9 | 33 ± 3* | 26 ± |
| Lean mass, g | 35 ± 1 | 38 ± 1 | 37 ± 2 | 35 ± 2 | 38 ± 2 | 34 ± 1 |
| Fluid mass, g | 323 ± 12 | 343 ± 9 | 332 ± 11 | 331 ± 15 | 332 ± 11 | 305 ± |
| LV weight, g | 1.07 ± 0.06† | 1.36 ± 0.1 | 1.26 ± 0.05 | 1.13 ± 0.03† | 1.13 ± 0.05† | 1.06 ± |
| RV weight, g | 0.22 ± 0.01† | 0.28 ± 0.02 | 0.22 + 0.01* | 0.23 ± 0.01* | 0.24 ± 0.01* | 0.20 ± |
| Lung weight, g | 1.53 ± 0.05* | 2.45 ± 0.05 | 1.94 ± 0.35 | 1.66 ± 0.13* | 1.48 ± 0.03* | 1.51 ± |
| LV weight/B.W., % | 0.21 ± 0.01† | 0.26 ± 0.01 | 0.24 ± 0.01 | 0.22 ± 0.01* | 0.23 ± 0.01* | 0.24 ± |
| RV weight/B.W., % | 0.04 ± 0.00* | 0.05 ± 0.01 | 0.04 ± 0.01† | 0.04 ± 0.00† | 0.04 ± 0.00* | 0.05 ± |
| Lung weight/B.W., % | 0.30 ± 0.01* | 0.48 ± 0.1 | 0.37 ± 0.07 | 0.32 ± 0.02* | 0.30 ± 0.01* | 0.33 ± 0.01 |
| Infarct size, % |  | 33 ± 4 | 30 ± 2 | 29 ± 2 | 31 ± 3 | 31 ± |

Values are mean ± SEM.
*$p < 0.05$,
†$p < 0.01$ vs vehicle treated

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims as provided.

---

What is claimed is:

1. A method for attenuating or delaying cardiac remodeling, said method comprising:
administering to a subject in need thereof an amount of a cardioprotective incretin compound (CIC) effective to prevent a deleterious effect on or improve at least one cardiac parameter in said subject, whereby cardiac remodeling is attenuated or delayed, wherein said subject has experienced, or is experiencing, cardiac remodeling following a myocardial insult; and wherein said CIC is exendin-3, exendin-4, an exendin-3 analog with GLP-1 receptor agonist activity or an exendin-4 analog with GLP-1 receptor agonist activity, and wherein said CIC is administered after the myocardial insult.

2. The method of claim 1, wherein said cardiac parameter is selected from the group consisting of left ventricular diastolic function, peak velocity ratio of the E wave and A wave (E/A ratio), left ventricular end diastolic pressure, cardiac output, cardiac contractility, left ventricular mass, left ventricular mass to body weight ratio, left ventricular volume, left atrial volume, left ventricular end diastolic dimension (LVEDD), left ventricular end systolic dimension (LVESD), infarct size, exercise capacity, exercise efficiency, and heart chamber size.

3. The method of claim 2, wherein said heart chamber size is not increased in dimension or wall thickness.

4. The method of claim 2, wherein said peak velocity ratio of the E wave and A wave (E/A ratio) is increased after myocardial infarction.

5. The method of claim 2, wherein said infarct size is decreased.

6. The method of claim 2, wherein said exercise capacity is increased.

7. The method of claim 2, wherein said exercise efficiency is increased.

8. The method of claim 2, wherein said cardiac output is normalized after myocardial infarction.

9. The method of claim 1, wherein said myocardial insult is the result of a condition selected from the group consisting of cardiac valve disease, myocardial infarction, cardiomyopathy, hypertension, infection, inflammation, surgery, genetic predisposition, volume overload, cor pulmonale and pulmonary hypertension.

10. The method of claim 9, wherein said cardiomyopathy is dilated cardiomyopathy, viral cardiomyopathy, or idiopathic cardiomyopathy.

11. The method of claim 1, wherein said subject is also suffering from diabetes.

12. The method of claim 1, wherein said cardioprotective incretin compound (CIC) is acutely administered to said subject.

13. The method of claim 1, wherein said cardioprotective incretin compound (CIC) is chronically administered to said subject.

14. The method of claim 1, wherein said cardioprotective incretin compound (CIC) is exendin-4.

15. The method of claim 1, wherein said cardioprotective incretin compound (CIC) is exendin-3.

16. The method of claim 1, wherein said exendin-3 analog with GLP-1 receptor agonist activity or said exendin-4 analog with GLP-1 receptor agonist activity is exendin-4(1-30), exendin-4(1-30) amide, exendin-4(1-28) amide, $^{14}$Leu, $^{25}$Phe exendin-4, $^{14}$Leu, $^{25}$Phe exendin-4(1-28) amide, or $^{14}$Leu, $^{22}$Ala, $^{25}$Phe exendin-4(1-28) amide.

17. The method of claim 1, wherein said exendin-3 analog with GLP-1 receptor agonist activity or said exendin-4 analog with GLP-1 receptor agonist activity is a peptide compound of the formula (I):

```
                                                (SEQ ID NO: 62)
Xaa1 Xaa2 Xaa3 Gly Thr Xaa6 Xaa7 Xaa8 Xaa9 Xaa10

Ser Lys Gln Xaa14 Glu Glu Glu Ala Val Arg Leu

Xaa22 Xaa23 Xaa24 Xaa25 Leu Lys Asn Gly Gly Xaa31

Ser Ser Gly Ala Xaa36 Xaa37 Xaa38 Xaa39,
``` wherein $Xaa_1$ is His, Arg or Tyr; $Xaa_2$ is Ser, Gly, Ala or Thr; $Xaa_3$ is Asp or Glu; $Xaa_6$ is Phe, Tyr or naphthylalanine; $Xaa_7$ is Thr or Ser; $Xaa_8$ is Ser or Thr; $Xaa_9$ is Asp or Glu; $Xaa_{10}$ is Leu, Ile, Val, pentylglycine or Met; $Xaa_{14}$ is Leu, Ile, pentylglycine, Val or Met; $Xaa_{22}$ is Phe, Tyr or naphthylalanine; $Xaa_{23}$ is Ile, Val, Leu, pentylglycine, tert-butylglycine or Met; $Xaa_{24}$ is Glu or Asp; $Xaa_{25}$ is Trp, Phe, Tyr, or naphthylalanine; $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and Xaa39 is Ser, Thr or Tyr; wherein the C-terminus of the peptide is modified by —Z, wherein Z is —OH or —NH$_2$; with the proviso that the compound is not exendin-3 or exendin-4.

18. The method of claim 1, wherein said exendin-3 analog with GLP-1 receptor agonist activity or said exendin-4 analog with GLP-1 receptor agonist activity is a peptide compound of the formula (II):

```
Xaa1 Xaa2 Xaa3 Gly Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

Xaa27 Xaa28,
``` wherein
$Xaa_1$ is His, Arg or Tyr;
$Xaa_2$ is Ser, Gly, Ala or Thr;
$Xaa_3$ is Ala, Asp or Glu;

Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa9 is Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala or Leu;
Xaa$_{22}$ is Ala, Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
Xaa$_{27}$ is Ala or Lys;
Xaa$_{28}$ is Ala or Asn;
wherein the C-terminus of the peptide is modified by —Z$_1$, wherein Z$_1$ is —OH or —NH$_2$, or wherein the C-terminus of the peptide further comprises Gly, Gly Gly (SEQ ID NO:63), Gly Gly Xaa$_{31}$ (SEQ ID NO:64), Gly Gly Xaa$_{31}$ Ser (SEQ ID NO:65), Gly Gly Xaa$_{31}$ Ser Ser (SEQ ID NO:66), Gly Gly Xaa$_{31}$ Ser Ser Gly (SEQ ID NO:67), Gly Gly Xaa$_{31}$ Ser Ser Gly Ala (SEQ ID NO:68), Gly Gly Xaa$_{31}$ Ser Ser Gly Ala Xaa$_{36}$ (SEQ ID NO:69), Gly Gly Xaa$_{31}$ Ser Ser Gly Ala Xaa$_{36}$ Xaa$_{37}$ (SEQ ID NO:70) or Gly Gly Xaa$_{31}$ Ser Ser Gly Ala Xaa$_{36}$ Xaa$_{37}$ Xaa$_{38}$ (SEQ ID NO:71); Xaa$_{31}$, Xaa$_{36}$, Xaa$_{37}$ and Xaa$_{38}$ are independently Pro, homoproline, 3Hyp, thioproline, N-alkylglycine, N-alkylpentylglycine or N-alkylalanine; and the C-terminus of the peptide is modified by —Z$_2$, wherein Z$_2$ is —OH or —NH$_2$; provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala.

19. The method of claim 1, wherein said exendin-3 analog with GLP-1 receptor agonist activity or said exendin-4 analog with GLP-1 receptor agonist activity is a peptide compound of formula (III):

Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{19}$ Xaa$_{20}$ Xaa$_{21}$ Xaa$_{22}$ Xaa$_{23}$ Xaa$_{24}$ Xaa$_{25}$ Xaa$_{26}$

Xaa$_{27}$ Xaa$_{28}$, wherein
Xaa$_1$ is His, Arg, Tyr, Ala, Norval, Val, or Norleu;
Xaa$_2$ is Ser, Gly, Ala or Thr;
Xaa$_3$ is Ala, Asp or Glu;
Xaa$_4$ is Ala, Norval, Val, Norleu or Gly;
Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa$_9$ is Ala, Norval, Val, Norleu, Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala or Leu;
Xaa$_{22}$ is Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
Xaa$_{27}$ is Ala or Lys;
Xaa$_{28}$ is Ala or Asn;
wherein the C-terminus of the peptide is modified by —Z$_1$, wherein Z$_1$ is —OH or NH$_2$, or wherein the C-terminus of the peptide further comprises Gly, Gly Gly, Gly Gly Xaa$_{31}$, Gly Gly Xaa$_{31}$ Ser (SEQ ID NO:72), Gly Gly Xaa$_{31}$ Ser Ser (SEQ ID NO:73), Gly Gly Xaa$_{31}$ Ser Ser Gly (SEQ ID NO:74), Gly Gly Xaa$_{31}$ Ser Ser Gly Ala (SEQ ID NO:75), Gly Gly Xaa$_{31}$ Ser Ser Gly Ala Xaa$_{36}$ (SEQ ID NO:76), Gly Gly Xaa$_{31}$ Ser Ser Gly Ala Xaa$_{36}$ Xaa$_{37}$ (SEQ ID NO:77), Gly Gly Xaa$_{31}$ Ser Ser Gly Ala Xaa$_{36}$ Xaa$_{37}$ Xaa$_{38}$ (SEQ ID NO:78) or Gly Gly Xaa$_{31}$ Ser Ser Gly Ala Xaa$_{36}$ Xaa$_{37}$ Xaa$_{38}$ Xaa$_{39}$ (SEQ ID NO:79); wherein Xaa$_{31}$, Xaa$_{36}$, Xaa$_{37}$ and Xaa$_{38}$ are independently Pro, homoproline, 3Hyp, 4Hyp, thioproline, N-alkylglycine, N-alkylpentylglycine or N-alkylalanine; Xaa$_{39}$ is Ser, Thr, Lys or Ala, and the C-terminus of the peptide is modified by —Z$_2$, wherein Z$_2$ is —OH or —NH$_2$; provided that no more than three of Xaa$_3$, Xaa$_4$, Xaa$_5$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$ Xaa$_{26}$, Xaa$_{27}$, and Xaa$_{28}$ are Ala; and provided also that, if Xaa$_1$ is His, Arg or Tyr, then at least one of Xaa$_3$, Xaa$_4$ and Xaa$_9$ is Ala.

20. The method of claim 1, wherein said cardioprotective incretin compound (CIC) is parenterally administered to said subject.

21. The method of claim 1, wherein cardioprotective incretin compound (CIC) is acutely administered to said subject.

22. The method of claim 1, wherein said CIC is administered after 72 hours after the myocardial insult.

23. A method for reducing atrial or ventricular remodeling, said method comprising:
administering to a subject in need thereof an amount of a cardioprotective incretin compound (CIC) effective to reduce atrial or ventricular remodeling, wherein said subject has experienced, or is experiencing, atrial or ventricular remodeling following a myocardial insult, and wherein said CIC is exendin-3, exendin-4, an exendin-3 analog with GLP-1 receptor agonist activity or an exendin-4 analog with GLP-1 receptor agonist activity, and wherein said CIC is administered after the myocardial insult.

24. The method of claim 23, wherein said CIC is administered after 72 hours after the myocardial insult.

* * * * *